(12) United States Patent
Chen et al.

(10) Patent No.: US 8,235,902 B2
(45) Date of Patent: Aug. 7, 2012

(54) SYSTEM AND METHOD FOR TISSUE CHANGE MONITORING DURING HIFU TREATMENT

(75) Inventors: Wo-Hsing Chen, Fishers, IN (US); Roy Carlson, New Palestine, IN (US); Clint C. Weis, Greenwood, IN (US); Ralf Seip, Indianapolis, IN (US); Narendra T. Sanghvi, Indianapolis, IN (US)

(73) Assignee: Focus Surgery, Inc., Indianapolis, IN (US)

( * ) Notice: Subject to any disclaimer, the term of this patent is extended or adjusted under 35 U.S.C. 154(b) by 1273 days.

(21) Appl. No.: 11/853,191

(22) Filed: Sep. 11, 2007

(65) Prior Publication Data

US 2009/0069677 A1     Mar. 12, 2009

(51) Int. Cl.
*A61B 8/00*     (2006.01)
(52) U.S. Cl. ......... 600/439; 600/407; 600/437; 600/427
(58) Field of Classification Search .................. 600/407, 600/437, 439, 471
See application file for complete search history.

(56) References Cited

U.S. PATENT DOCUMENTS

| | | |
|---|---|---|
| 4,005,258 A | 1/1977 | Dory |
| 4,005,382 A | 1/1977 | Beaver |
| 4,012,952 A | 3/1977 | Dory |
| 4,063,451 A | 12/1977 | Dory |
| 4,074,564 A | 2/1978 | Anderson |
| 4,084,582 A | 4/1978 | Nigam |
| 4,114,456 A | 9/1978 | Dory |
| 4,161,121 A | 7/1979 | Zitelli et al. |
| 4,174,634 A | 11/1979 | Dory |
| 4,183,249 A | 1/1980 | Anderson |
| 4,207,901 A | 6/1980 | Nigam |
| 4,209,022 A | 6/1980 | Dory |
| 4,209,706 A | 6/1980 | Nunan |
| 4,223,560 A | 9/1980 | Glenn |
| 4,227,417 A | 10/1980 | Glenn |
| 4,231,373 A | 11/1980 | Waxman et al. |
| 4,241,412 A | 12/1980 | Swain |
| 4,241,610 A | 12/1980 | Anderson |
| 4,248,090 A | 2/1981 | Glenn |
| 4,257,271 A | 3/1981 | Glenn |
| 4,274,421 A | 6/1981 | Dory |
| 4,274,422 A | 6/1981 | Anderson et al. |
| 4,281,661 A | 8/1981 | Dory |
| 4,290,310 A | 9/1981 | Anderson |

(Continued)

FOREIGN PATENT DOCUMENTS

CA        1332441        10/1994

(Continued)

OTHER PUBLICATIONS

R. Seip, et al., "Sonablate® 500: A Novel Platform for Transrectal Image-Guided HIFU Treatment of Localized Prostate Cancer," presented at the 32nd Annual Symposium of the *Ultrasonic Industry Association* (UIA), Oct. 2002, 28 pgs.

(Continued)

*Primary Examiner* — Tse Chen
*Assistant Examiner* — Joel F Brutus
(74) *Attorney, Agent, or Firm* — William J. McNichol, Jr.; Reed Smith LLP

(57) ABSTRACT

A method and apparatus is disclosed for determining the presence of tissue change due to exposure to HIFU Therapy.

18 Claims, 16 Drawing Sheets

U.S. PATENT DOCUMENTS

| | | |
|---|---|---|
| 4,317,370 A | 3/1982 | Glenn |
| 4,324,258 A | 4/1982 | Huebscher et al. |
| 4,325,381 A | 4/1982 | Glenn |
| 4,327,738 A | 5/1982 | Green et al. |
| 4,340,944 A | 7/1982 | Dory |
| 4,341,120 A | 7/1982 | Anderson |
| 4,378,596 A | 3/1983 | Clark |
| 4,407,293 A | 10/1983 | Suarez, Jr. et al. |
| 4,410,826 A | 10/1983 | Waxman et al. |
| 4,413,630 A | 11/1983 | Anderson et al. |
| 4,418,698 A | 12/1983 | Dory |
| 4,449,199 A | 5/1984 | Daigle |
| 4,530,358 A | 7/1985 | Forssmann et al. |
| 4,586,512 A | 5/1986 | Do-huu et al. |
| 4,617,931 A | 10/1986 | Dory |
| 4,620,546 A | 11/1986 | Aida et al. |
| 4,638,436 A | 1/1987 | Badger et al. |
| 4,658,828 A | 4/1987 | Dory |
| 4,664,121 A | 5/1987 | Sanghvi et al. |
| 4,727,875 A | 3/1988 | Dory |
| 4,807,633 A | 2/1989 | Fry |
| 4,856,107 A | 8/1989 | Dory |
| 4,858,613 A | 8/1989 | Fry et al. |
| 4,917,096 A | 4/1990 | Englehard et al. |
| 4,922,917 A | 5/1990 | Dory |
| 4,942,878 A | 7/1990 | Dory |
| 4,945,898 A | 8/1990 | Pell et al. |
| 4,951,653 A | 8/1990 | Fry et al. |
| 4,955,365 A | 9/1990 | Fry et al. |
| 4,991,151 A | 2/1991 | Dory |
| 4,995,012 A | 2/1991 | Dory |
| RE33,590 E | 5/1991 | Dory |
| 5,033,456 A | 7/1991 | Pell et al. |
| 5,036,855 A | 8/1991 | Fry et al. |
| 5,054,470 A | 10/1991 | Fry et al. |
| 5,065,761 A | 11/1991 | Pell |
| 5,080,101 A | 1/1992 | Dory |
| 5,080,102 A | 1/1992 | Dory |
| 5,111,822 A | 5/1992 | Dory |
| 5,117,832 A | 6/1992 | Sanghvi et al. |
| 5,134,988 A | 8/1992 | Pell et al. |
| 5,143,073 A | 9/1992 | Dory |
| 5,143,074 A | 9/1992 | Dory |
| 5,149,319 A | 9/1992 | Unger |
| 5,150,711 A | 9/1992 | Dory |
| 5,150,712 A | 9/1992 | Dory |
| 5,158,070 A | 10/1992 | Dory |
| 5,195,509 A | 3/1993 | Rentschler et al. |
| 5,215,680 A | 6/1993 | D'Arrigo |
| 5,219,401 A | 6/1993 | Cathignol et al. |
| 5,247,935 A | 9/1993 | Cline et al. |
| 5,295,484 A | 3/1994 | Marcus et al. |
| 5,316,000 A | 5/1994 | Chapelon et al. |
| 5,354,258 A | 10/1994 | Dory |
| 5,391,197 A | 2/1995 | Burdette et al. |
| 5,409,002 A | 4/1995 | Pell |
| 5,409,006 A | 4/1995 | Buchholtz et al. |
| 5,431,621 A | 7/1995 | Dory |
| 5,443,069 A | 8/1995 | Schaetzle |
| 5,470,350 A | 11/1995 | Buchholtz et al. |
| 5,492,126 A | 2/1996 | Hennige et al. |
| 5,520,188 A | 5/1996 | Hennige et al. |
| 5,573,497 A | 11/1996 | Chapelon |
| 5,601,526 A | 2/1997 | Chapelon et al. |
| 5,620,479 A | 4/1997 | Diederich |
| 5,630,837 A | 5/1997 | Crowley |
| 5,643,179 A | 7/1997 | Fujimoto et al. |
| 5,665,054 A | 9/1997 | Dory |
| 5,676,692 A | 10/1997 | Sanghvi et al. |
| 5,722,411 A | 3/1998 | Suzuki et al. |
| 5,725,482 A | 3/1998 | Bishop |
| 5,762,066 A | 6/1998 | Law et al. |
| 5,769,790 A * | 6/1998 | Watkins et al. ............... 600/439 |
| 5,817,021 A | 10/1998 | Reichenberger |
| 5,840,031 A | 11/1998 | Crowley |
| 5,873,902 A | 2/1999 | Sanghvi et al. |
| 5,879,314 A | 3/1999 | Peterson et al. |
| 5,882,302 A | 3/1999 | Driscoll, Jr. et al. |
| 5,906,580 A | 5/1999 | Kline-Schoder et al. |
| 5,993,389 A | 11/1999 | Driscoll, Jr. et al. |
| 6,016,452 A | 1/2000 | Kasevich |
| 6,023,660 A | 2/2000 | Dory |
| 6,028,547 A | 2/2000 | Dory |
| 6,083,159 A | 7/2000 | Driscoll, Jr. et al. |
| 6,093,883 A | 7/2000 | Sanghvi et al. |
| 6,126,619 A | 10/2000 | Peterson et al. |
| 6,186,951 B1 | 2/2001 | Lizzi et al. |
| 6,217,530 B1 | 4/2001 | Martin et al. |
| 6,334,846 B1 | 1/2002 | Ishibashi et al. |
| 6,375,634 B1 | 4/2002 | Carroll |
| 6,425,867 B1 | 7/2002 | Vaezy et al. |
| 6,500,133 B2 | 12/2002 | Martin et al. |
| 6,508,774 B1 | 1/2003 | Acker et al. |
| 6,511,430 B1 * | 1/2003 | Sherar et al. ............... 600/443 |
| 6,575,956 B1 | 6/2003 | Brisken et al. |
| 6,618,620 B1 | 9/2003 | Freundlich et al. |
| 6,626,855 B1 | 9/2003 | Weng et al. |
| 6,656,136 B1 | 12/2003 | Weng et al. |
| 6,666,835 B2 | 12/2003 | Martin et al. |
| 6,676,601 B1 | 1/2004 | Lacoste et al. |
| 6,685,639 B1 | 2/2004 | Wang et al. |
| 6,685,640 B1 | 2/2004 | Fry et al. |
| 6,694,170 B1 | 2/2004 | Mikus et al. |
| 6,716,184 B2 | 4/2004 | Vaezy et al. |
| 6,772,490 B2 | 8/2004 | Toda |
| 6,812,204 B1 | 11/2004 | McHale et al. |
| 6,846,290 B2 | 1/2005 | Lizzi et al. |
| 6,875,176 B2 | 4/2005 | Mourad et al. |
| 2001/0008758 A1 | 7/2001 | McHale et al. |
| 2001/0014780 A1 | 8/2001 | Martin et al. |
| 2002/0035361 A1 | 3/2002 | Houser et al. |
| 2002/0095087 A1 | 7/2002 | Mourad et al. |
| 2002/0102216 A1 | 8/2002 | Lanza et al. |
| 2002/0193785 A1 | 12/2002 | Naghavi et al. |
| 2003/0018358 A1 | 1/2003 | Saadat |
| 2003/0028111 A1 | 2/2003 | Vaezy et al. |
| 2003/0040698 A1 | 2/2003 | Makin et al. |
| 2003/0060736 A1 | 3/2003 | Martin et al. |
| 2003/0171700 A1 | 9/2003 | Martin et al. |
| 2003/0191396 A1 | 10/2003 | Sanghvi et al. |
| 2003/0204141 A1 | 10/2003 | Nock et al. |
| 2003/0229331 A1 | 12/2003 | Brisken et al. |
| 2004/0030227 A1 | 2/2004 | Littrup et al. |
| 2004/0030268 A1 | 2/2004 | Weng et al. |
| 2004/0039312 A1 | 2/2004 | Hillstead et al. |
| 2004/0059220 A1 | 3/2004 | Mourad et al. |
| 2004/0071664 A1 | 4/2004 | McHale et al. |
| 2004/0106870 A1 | 6/2004 | Mast |
| 2004/0106880 A1 | 6/2004 | Weng et al. |
| 2004/0133192 A1 | 7/2004 | Houser et al. |
| 2004/0167403 A1 | 8/2004 | Nightingale et al. |
| 2004/0210289 A1 | 10/2004 | Wang et al. |
| 2004/0254419 A1 | 12/2004 | Wang et al. |
| 2004/0264293 A1 | 12/2004 | Laugharn, Jr. et al. |
| 2005/0015009 A1 | 1/2005 | Mourad et al. |
| 2005/0025797 A1 | 2/2005 | Wang et al. |
| 2005/0038340 A1 | 2/2005 | Vaezy et al. |
| 2005/0074407 A1 | 4/2005 | Smith |
| 2005/0154308 A1 | 7/2005 | Quistgaard et al. |
| 2005/0154309 A1 | 7/2005 | Etchells et al. |
| 2005/0154431 A1 | 7/2005 | Quistgaard et al. |
| 2005/0193451 A1 | 9/2005 | Quistgaard et al. |
| 2005/0240127 A1 | 10/2005 | Seip et al. |
| 2007/0010805 A1 | 1/2007 | Fedewa et al. |
| 2007/0038096 A1 | 2/2007 | Seip |
| 2007/0219448 A1 | 9/2007 | Seip et al. |
| 2008/0039724 A1 | 2/2008 | Seip |
| 2008/0077056 A1 | 3/2008 | Kagosaki |

FOREIGN PATENT DOCUMENTS

| | | |
|---|---|---|
| CA | 1338240 | 4/1996 |
| EP | 0596513 | 11/1994 |
| WO | WO 93/16641 | 9/1993 |
| WO | WO 97/47881 A1 | 12/1997 |
| WO | WO 98/58588 | 12/1998 |
| WO | WO 99/49788 | 10/1999 |
| WO | WO 01/28623 A2 | 4/2001 |

| | | | |
|---|---|---|---|
| WO | WO 01/28623 A3 | 4/2001 | |
| WO | WO 01/82777 A2 | 11/2001 | |
| WO | WO 01/82777 A3 | 11/2001 | |
| WO | WO 01/82778 A2 | 11/2001 | |
| WO | WO 02/24050 A2 | 3/2002 | |
| WO | WO 2005/107601 A2 | 11/2005 | |
| WO | 2006119572 A1 | 11/2006 | |
| WO | 2006129099 A1 | 12/2006 | |
| WO | 2007102161 A2 | 9/2007 | |

OTHER PUBLICATIONS

T. Uchida, et al., "Clinical Outcome of High-Intensity Focused Ultrasound (HIFU) for the Treatment of Localized Prostate Cancer: 5-Years Experience", to appear in the *Proc. of the International Symposium on Therapeutic Ultrasound*, 2004, 1 pg. (Abstract).

J.S. Tan, et al., "Design of Focused Ultrasound Phased Arrays for Prostate Treatment," IEEE Ultrasonics Symposium Proceedings, Puerto Rico , 2000, 5 pgs.

T. Gardner, et al., "HIFU Prostatectomy for Prostate Cancer: The USA Experience", to appear in the *Proc. of the International Symposium on Therapeutic Ultrasound*, 2004, 1 pg. (Abstract).

J. C. Rewcastle, Ph.D., "High Intensity Focused Ultrasound for Prostate Cancer: Clinical Results and Technical Evolution", Whitepaper, 2004, 14 pgs.

T. Uchida, et al., "Transrectal High-Intensity Focused Ultrasound for Treatment of Patients with Stage T1b-2N0M0 Localized Prostate Cancer: A Preliminary Report", *Japanese Journal of Endourology and ESWL*, vol. 16, pp. 108-114, 2003.

T. Uchida, et al., "Transrectal High-Intensity Focused Ultrasound for Treatment of Patients with Stage T1b-2N0M0 Localized Prostate Cancer: A Preliminary Report", *Urology*, 2002, pp. 394-399.

T. Uchida, et al., "Transrectal High Intensity Focused Ultrasound for the Treatment of Localized Prostate Cancer," *International Symposium on Therapeutic Ultrasound*, Seattle, 2002, 9 pgs.

S. Madersbacher, et al., "Effect of High-Intensity Focused Ultrasound on Human Prostate Cancer in Vivo", *Cancer Research* 55, Aug. 1995, pp. 3346-3351.

N. T. Sanghvi, et al., "Noninvasive Surgery of Prostate Tissue by High Intensity Focused Ultrasound: An Updated Report", *European Journal of Ultrasound*, vol. 9; 1999, pp. 19-29.

T. Uchida, et al., "Clinical Outcome of High-Intensity Focused Ultrasound for Treating Benign Prostatic Hyperplasia: Preliminary Report", *Urology*, 1998, pp. 66-71.

L. D. Sullivan, et al., "Early Experience with High-Intensity Focused Ultrasound for the Treatment of Benign Prostatic Hypertrophy", *British Journal of Urology*, 79; 1997, pp. 172-176.

N. T. Sanghvi, et al., "Noninvasive Surgery of Prostate Tissue by High-Intensity Focused Ultrasound", *IEEE Transactions on Ultrasonics, Ferroelectrics, and Frequency Control*. vol. 43, No. 6, Nov. 1996, pp. 1099-1110.

S. Madersbacher, et al., "High-Intensity Focused Ultrasound in Urology", *Japanese Journal of Endourology and ESWL*, vol. 9, No. 1, 1996, pp. 5-15.

F. Fry, et al., "Ultrasound and Microbubbles: Their Generation, Detection and Potential Utilization in Tissue and Organ Therapy—Experimental", *Ultrasound in Medicine & Biology*, vol. 21, No. 9, 1995, pp. 1227-1237.

S. Madersbacher, et al., "Tissue Ablation in Benign Prostatic Hyperplasia with High Intensity Focused Ultrasound", *J. Urology*, vol. 152, Dec. 1994, pp. 1956-1961.

R. S. Foster, et al., "High-Intensity Focused Ultrasound for the Treatment of Benign Prostatic Hypertrophy", *Seminars in Urology*, vol. XII, No. 3, pp. 200-204, Aug. 1994.

S. Umemura, et al., "Coagulation of Swine Liver and Canine Prostate with a Prototype Split-Focus Transducer", *IEEE Ultrasonics Symposium*, 1999, 4 pgs.

J. Wu, et al., "Experimental Studies of Using a Split Beam Transducer for Prostate Cancer Therapy in Comparison to Single Beam Transducer", *IEEE Ultrasonics Symposium*, 1999, 4 pgs.

T. Uchida, "Localized Prostate Cancer Treatment by High Intensity Focused Ultrasound (HIFU)", Translated and updated from *The Journal of Highly Advanced Medical Technology*, vol. 15 Mar. 2000, 1 pg.

R. Seip, et al., "Comparison of Split-Beam Transducer Geometries and Excitation Configurations for Transrectal Prostate HIFU Treatments", *IEEE Ultrasonics Symposium Proceedings*, 2001, 4 pgs.

R. Seip, et al., "High-Intensity Focused Ultrasound (HIFU) Phased Arrays: Recent Developments in Transrectal Transducers and Driving Electronics Design," *Third International Symposium on Therapeutic Ultrasound*, Lyon, France, Jun. 2003, 6 pgs.

R. Seip, et al., "High-Intensity Focused Ultrasound (HIFU) Phased Arrays: Recent Developments in Transrectal Transducers and Driving Electronics Design," *Third International Symposium on Therapeutic Ultrasound*, Lyon, France, Jun. 2003 (Poster).

K. Ishida, et al., "Development and animal experiment of variable focusing HIFU system for prostate cancer treatment," *Proc. of the International Symposium on Therapeutic Ultrasound*, 2003, 6 pgs.

K. Ishida, et al., "Development and animal experiment of variable focusing HIFU system for prostate cancer treatment," *Proc. of the International Symposium on Therapeutic Ultrasound*, 2003, 18 pgs.

R. Seip, et al., "Annular and Cylindrical Phased Array Geometries for Transrectal High-Intensity Focused Ultrasound (HIFU) using PZT and Piezocomposite Materials," ISTU 4 Conference, Oct. 2004, Kyoto, Japan, 3 pgs.

R. Seip, et al., "High-Intensity Focused Ultrasound (HIFU) Multiple Lesion Imaging: Comparison of Detection Algorithms for Real-Time Treatment Control," *IEEE Ultrasonics Symposium Proceedings*, Munich, Germany, 2002, pp. 1395-1398.

R. Seip, et al., "Real-time Detection of Multiple Lesions during High Intensity Focused Ultrasound (HIFU) Treatments," *International Symposium on Therapeutic Ultrasound*, 2002, 8 pgs.

N.T. Sanghvi, et al., "Decision Theory Applied to High-Intensity Focused Ultrasound (HIFU) Treatment Evaluation," 2003 AIUM Annual Meeting, Jun. 1-4, 2003, Montreal, Quebec, Canada, 24 pgs.

W. Chen, et al., "The Detection and Exclusion of Prostate Neuro-Vascular Bundle (NVB) in Automated HIFU Treatment Planning Using a Pulsed-Wave Doppler Ultrasound System," 2004 ISTU Conference, Kyoto, Japan, 3 pgs.

R. Seip, et al., "Transurethral High Intensity Focused Ultrasound: Catheter Based Prototypes and Experimental Results," *IEEE Ultrasonics Symposium Proceedings*, Puerto Rico, 2000, 4 pgs.

J. Tavakkoli, et al., "A Laparoscopic HIFU Probe for Kidney Ablation Prior to Partial Nephrectomy," *IEEE Ultrasonics Symposium Proceedings*, Atlanta, 2001, 4 pgs.

N.T. Sanghvi, et al., "Laparoscopically Delivered HIFU for Partial Renal Ablation," 17th International Congress on Acoustics, Sep. 2-7, 2001, Rome, Italy, 2 pgs.

J. Tavakkoli, et al., "Laparoscopic High Intensity Focused Ultrasound: Application to Kidney Ablation," *International Symposium on Therapeutic Ultrasound*, Seattle, 2002, 9 pgs.

J. Tavakkoli, et al., "A Laparoscopic HIFU Probe with Integrated Phased Array Ultrasound Imaging," *Third International Symposium on Therapeutic Ultrasound*, Jun. 2003, Lyon, France, 6 pgs.

J. Tavakkoli, et al., "A Laparoscopic HIFU Probe with Integrated Phased Array Ultrasound Imaging," *International Symposium on Therapeutic Ultrasound*, 2003 (Poster).

R. Seip, et al., "Automated HIFU Treatment Planning and Execution based on 3D Modeling of the Prostate, Urethra, and Rectal Wall", 2004 IEEE Ultrasonics Symposium Proceedings, 4 pgs.

R. Seip, et al., "Automated HIFU Treatment Planning and Execution based on 3D Modeling of the Prostate, Urethra, and Rectal Wall", 2004 IEEE Ultrasonics Symposium Proceedings (Poster).

J.S. Tan, et al., "Ultrasound Phased Arrays for Prostate Treatment", *J. Acoust. Soc. Am.*, vol. 109, No. 6, Jun. 2001, pp. 3055-3064.

R. Seip, et al., "Feasibility Study for the Treatment of Brachytherapy Failure Prostate Cancer using High-Intensity Focused Ultrasound," *Third International Symposium on Therapeutic Ultrasound*, Lyon, France, Jun. 2003, 6 pgs.

M. Bailey, et al., "Caviation Detection and Suppression in HIFU," *Proc. of the International Symposium on Therapeutic Ultrasound*, 2003, 1 pg. (Poster).

The American Society for Therapeutic Radiology and Oncology Consensus Panel, "Consensus Statement: Guidelines for PSA Following Radiation Therapy," Int. J. Radiation Oncology Biol. Phys., vol. 37, No. 5, 1997, pp. 1035-1041.

N.T. Sanghvi, et al., "Total Prostate Ablation for the Treatment of Localized Prostate Cancer Using Image Guided HIFU," presented at the 2002 IEEE Ultrasonics Symposium. (Poster).

J. C. Rewcastle, Ph.D., "High Intensity Focused Ultrasound for Prostate Cancer: 2006 Technology and Outcome Update", Whitepaper, 2006, 14 pgs.

HIFU Technology Pte. Ltd., The Haifu Knife Model-JC Focused Ultrasound Tumor Therapeutic System, undated, 1 page.

* cited by examiner

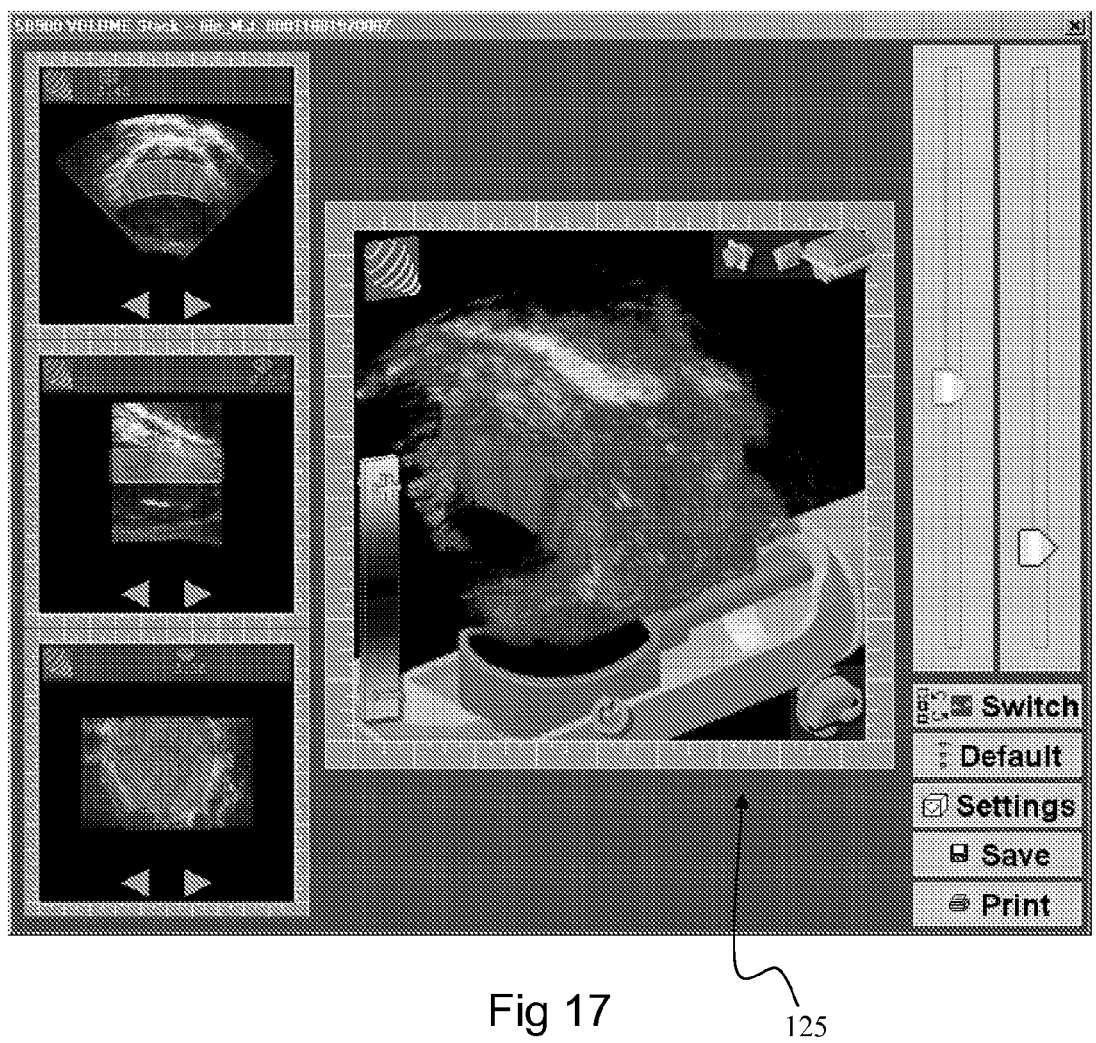
Fig 17     125

SYSTEM AND METHOD FOR TISSUE CHANGE MONITORING DURING HIFU TREATMENT

FIELD OF THE INVENTION

The present invention relates to an apparatus and related methods for the treatment of tissue, and in particular, for the non-invasive treatment of diseased tissue.

BACKGROUND AND SUMMARY OF THE INVENTION

Several techniques have been used in the past for the treatment of tissue including diseased tissue, such as cancer, to remove, destroy, or otherwise minimize the growth of the diseased tissue. For example, traditional methods of treating diseased prostate tissue include high intensity focused ultrasound ("HIFU"), radiation, surgery, Brachytherapy, cryoablation, hormonal therapy, and chemotherapy. Described herein are improved apparatus and methods for treating tissue with HIFU.

Although the techniques, methods, and apparatus discussed herein have applicability to the treatment of tissue in general, this discussion will focus primarily on the treatment of prostate tissue including Benign Prostatic Hyperplasia (BPH) and prostatic cancer. However, the disclosed apparatus and methods will find applications in localization and treatment of a wide range of diseases which manifest themselves in a localized or "focal" manner, including cancers of the breast, brain, liver, and kidney. As explained herein, the disclosed apparatus uses an intracavity probe which will be particularly useful for focal diseases which are accessible to a transesophageal, laparoscopic or transvaginal probe. Such diseases include esophageal cancer, cancer in the trachea and urethra, ulcers in the stomach and duodenum, and pancreatic cancer. Moreover, a transvaginal probe according to the present invention will provide a minimally invasive sterilization procedure on an outpatient basis, as well as therapy for fibroids, and endometrial ablation. Additionally, in the case of a transducer with multiple focal lengths, blood vessels may be selectively targeted to effect coagulation and cauterization of internal bleeding.

As used herein the term "HIFU Therapy" is defined as the provision of high intensity focused ultrasound to a portion of tissue at or proximate to a focus of a transducer. It should be understood that the transducer may have multiple foci and that HIFU Therapy is not limited to a single focus transducer, a single transducer type, or a single ultrasound frequency. As used herein the term "HIFU Treatment" is defined as the collection of one or more HIFU Therapies. A HIFU Treatment may be all of the HIFU Therapies administered or to be administered, or it may be a subset of the HIFU Therapies administered or to be administered. As used herein the term "HIFU System" is defined as a system that is at least capable of providing a HIFU Therapy.

In an exemplary embodiment of the present disclosure, an apparatus for treating tissue in a treatment region is provided. The apparatus comprising a transducer which is positionable proximate to the tissue and a positioning member coupled to the transducer and configured to position the transducer. The transducer being configured to emit ultrasound energy and to receive ultrasound energy. The apparatus further comprising a controller operably coupled to the transducer and to the positioning member. The controller being configured to position the transducer with the positioning member and to operate the transducer in an imaging mode wherein images of the tissue in the treatment region are obtained from ultrasound energy sensed by the transducer and in a therapy mode wherein a plurality of treatment sites are treated with a HIFU Therapy with the transducer. The controller being further configured to monitor a plurality of regions of interest in the treatment region and to determine a tissue change value for each region of interest based on a frequency analysis of at least two images of the plurality of images. Each region of interest corresponding to a multi-dimensional portion in each of the at least two images.

In another exemplary embodiment of the present disclosure, an apparatus for treating tissue in a treatment region is provided. The apparatus comprising a transducer which is positionable proximate to the tissue, the transducer being configured to emit ultrasound energy and to receive ultrasound energy; a positioning member coupled to the transducer and configured to position the transducer; and a controller operably coupled to the transducer and to the positioning member. The controller including means for determining a tissue change value for a region of interest in the treatment region.

In a further exemplary embodiment of the present disclosure, a method of providing treatment to a treatment region of tissue is provided. The method comprising the steps of acquiring a first image including a treatment site prior to a direct treatment with a HIFU Therapy, performing the direct treatment of the treatment site with the HIFU Therapy, acquiring a second image including the treatment site subsequent to the direct treatment, and determining a tissue change value in a region of interest of the tissue based on a first power spectrum of a portion of the first image corresponding to the region of interest and a second power spectrum of a portion of the second image corresponding to the region of interest. The first image being a multi-dimensional image. The second image being a multi-dimensional image. The region of interest including the treatment site.

In still another exemplary embodiment of the present disclosure, a method of providing treatment to a treatment region of tissue is provided. The method comprising the steps of: monitoring a level of a tissue change in a region of interest of the treatment region due to an indirect heating of the tissue in the region of interest in response to a direct treatment of at least one treatment sites with the HIFU Therapy in the treatment region outside of the region of interest and determining whether to provide a direct treatment with the HIFU Therapy to a treatment site within the region of interest based on the level of the tissue change. The level of the tissue change being determined by a comparison of the power spectra of at least two images including the region of interest.

In still a further exemplary embodiment of the present disclosure, a method of providing treatment to a treatment region of tissue is provided. The method comprising the steps of: performing acquiring a first image including a treatment site prior to a direct treatment with a HIFU Therapy, the first image being a multi-dimensional image; performing the direct treatment of the treatment site with the HIFU Therapy; acquiring a second image including the treatment site subsequent to the direct treatment, the second image being a multi-dimensional image; determining an indication of a tissue change in a region of interest of the tissue from a frequency domain analysis of the first image and the second image; and providing a color-coded visual indicator on an image of the treatment region. The color-coded visual indicator providing an indication of a degree of tissue change.

Additional features of the present invention will become apparent to those skilled in the art upon consideration of the following detailed description of the illustrative embodiments exemplifying the best mode of carrying out the invention as presently perceived.

BRIEF DESCRIPTION OF THE DRAWINGS

The detailed description of the drawings particularly refers to the accompanying figures in which:

FIG. 17 is an exemplary screen shot of the display of the HIFU System of FIG. 1 illustrating three-dimensional volumetric image including visual indicators of the tissue change.

DETAILED DESCRIPTION OF THE DRAWINGS

Figure 1:
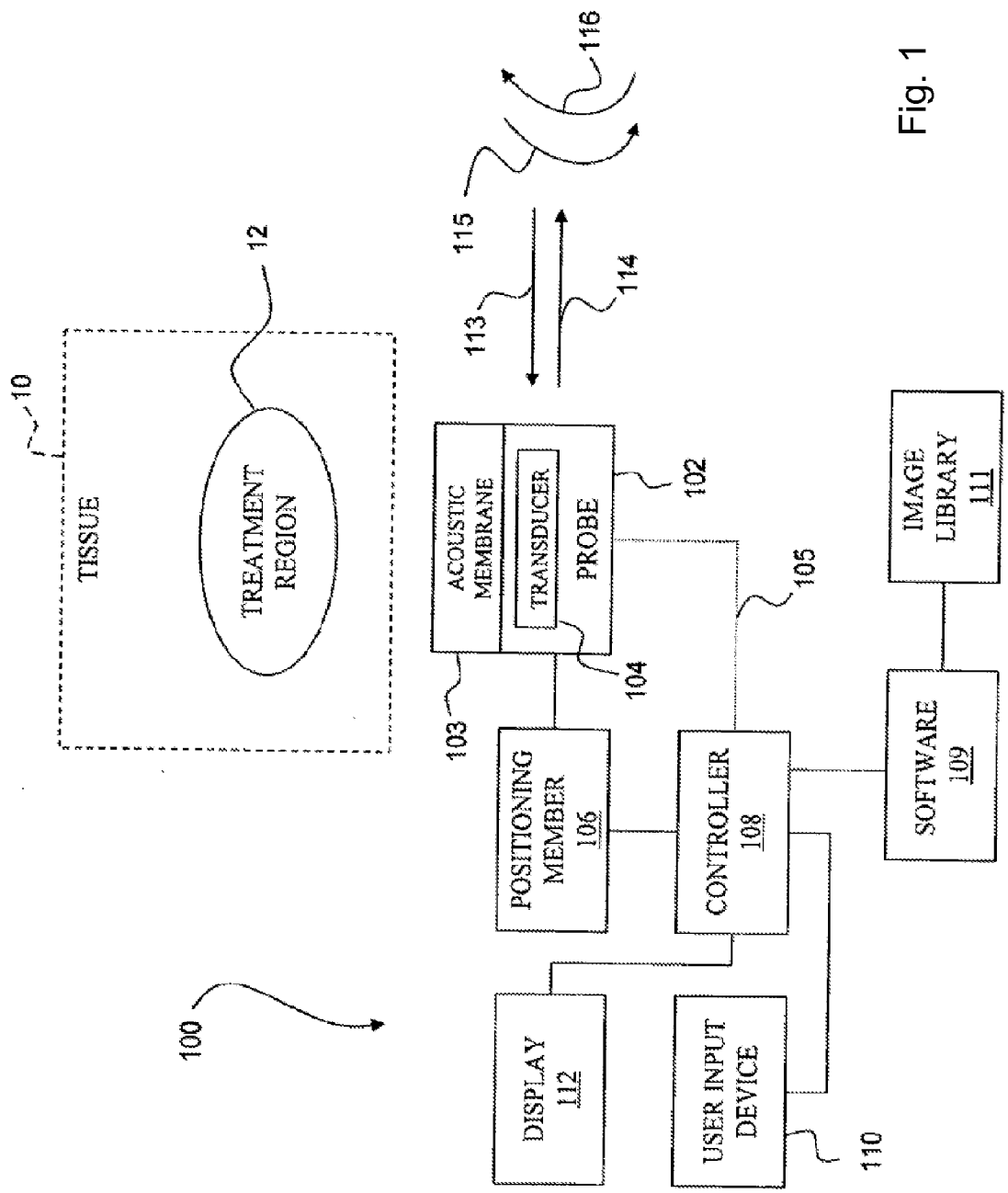
FIG. 1 is schematic view of an exemplary HIFU System of the present invention, the HIFU System being capable of imaging the tissue of the patient and to provide HIFU Therapy to at least a portion of the tissue at or proximate to a focus of a transducer of the HIFU System.

An exemplary HIFU System 100 is shown in FIG. 1. HIFU System 100 includes a probe 102 having a transducer member 104, a positioning member 106, a controller 108 operably coupled to probe 102 and the positioning member 106, a user input device 110 (such as keyboard, trackball, mouse, and/or touch screen), and a display 112. Probe 102 is operably connected to controller 108 through positioning member 106. However, as indicated by line 105 probe 102 may be directly connected with controller 108. Positioning member 106 is configured to linearly position transducer member 104 along directions 113, 114 and to angularly position transducer member 104 in directions 115, 116.

Transducer member 104 is positioned generally proximate to a region of tissue 10. In the case of the prostate, transducer 104 is positioned generally proximate to the prostate by the transrectal insertion of probe 102. Transducer member 104 is moved by positioning member 106 and controlled by controller 108 to provide imaging of at least a portion of tissue 10 including at least one treatment region 12 and to provide HIFU Therapy to portions of the tissue within at least one treatment region 12. As such, HIFU System 100 may operate in an imaging mode wherein at least a portion of tissue 10 may be imaged and in a therapy mode wherein HIFU Therapy is provided to portions of tissue 10 within at least one treatment region. As stated herein, treatment region 12 is defined as one or more portions of tissue which are to be treated during a HIFU Treatment. Treatment region 12 is illustratively shown as a continuous region. However, a treatment region might involve two or more distinct regions.

In one embodiment, transducer member 104 is a single crystal two element transducer. An exemplary transducer is disclosed in U.S. Pat. No. 5,117,832, the disclosure of which is expressly incorporated herein by reference. In a preferred embodiment, transducer 104 is capable of providing imaging of at least a portion of tissue 10 in an imaging mode and of providing HIFU Therapy to at least a portion of tissue 10 within treatment region 12 in a therapy mode.

However, the present invention is not limited to the type of transducer implemented. On the contrary, various transducer geometries having a single focus or multiple foci and associated controls may be used including transducers which are phased arrays, such as the transducers disclosed in pending U.S. patent application Ser. No. 11/070,371, filed Mar. 2, 2005, titled "Ultrasound Phased Arrays," the disclosure of which is expressly incorporated herein by reference. Additional exemplary transducers and associated controls are disclosed in U.S. Pat. No. 5,762,066; U.S. Abandoned patent application Ser. No. 07/840,502 filed Feb. 21, 1992; U.S. Pat. No. 5,036,855; U.S. Pat. No. 5,492,126; U.S. Pat. No. 6,685, 640, U.S. patent application Ser. No. 11/463,692 filed Aug. 10, 2006, the disclosure each of which is expressly incorporated herein by reference.

In one embodiment, a portion of probe 102 is covered by an acoustic membrane 103. Acoustic membrane 103 is an expandable membrane whose overall size is increased by placing a fluid on an interior of acoustic membrane 103. In one embodiment, the fluid is water or a generally acoustic transparent material and is provided by a reservoir or a chiller. The fluid may be used to remove heat from proximate to transducer 104 as well as expanding acoustic membrane 103. In one embodiment, acoustic membrane 103 is expanded such that it contacts or generally is adjacent to the surrounding tissue, such as a rectal wall. In one embodiment, acoustic membrane 103 is a condom placed over a tip of probe 102, sealed with o-rings, and filled with water. Exemplary acoustic membranes and details of their operation in relation to respective other portions of exemplary HIFU Systems are provided in U.S. Pat. No. 5,762,066, U.S. Pat. No. 5,993,389, and U.S. Provisional Patent Application Ser. No. 60/686,499, filed Jun. 1, 2005, the disclosures each of which are expressly incorporated by reference herein.

In one embodiment, controller 108 is configured to execute one or more of the methods discussed herein. In one embodiment, at least a portion of each method executed by controller 108 is provided as a portion of software 109.

Figure 2:
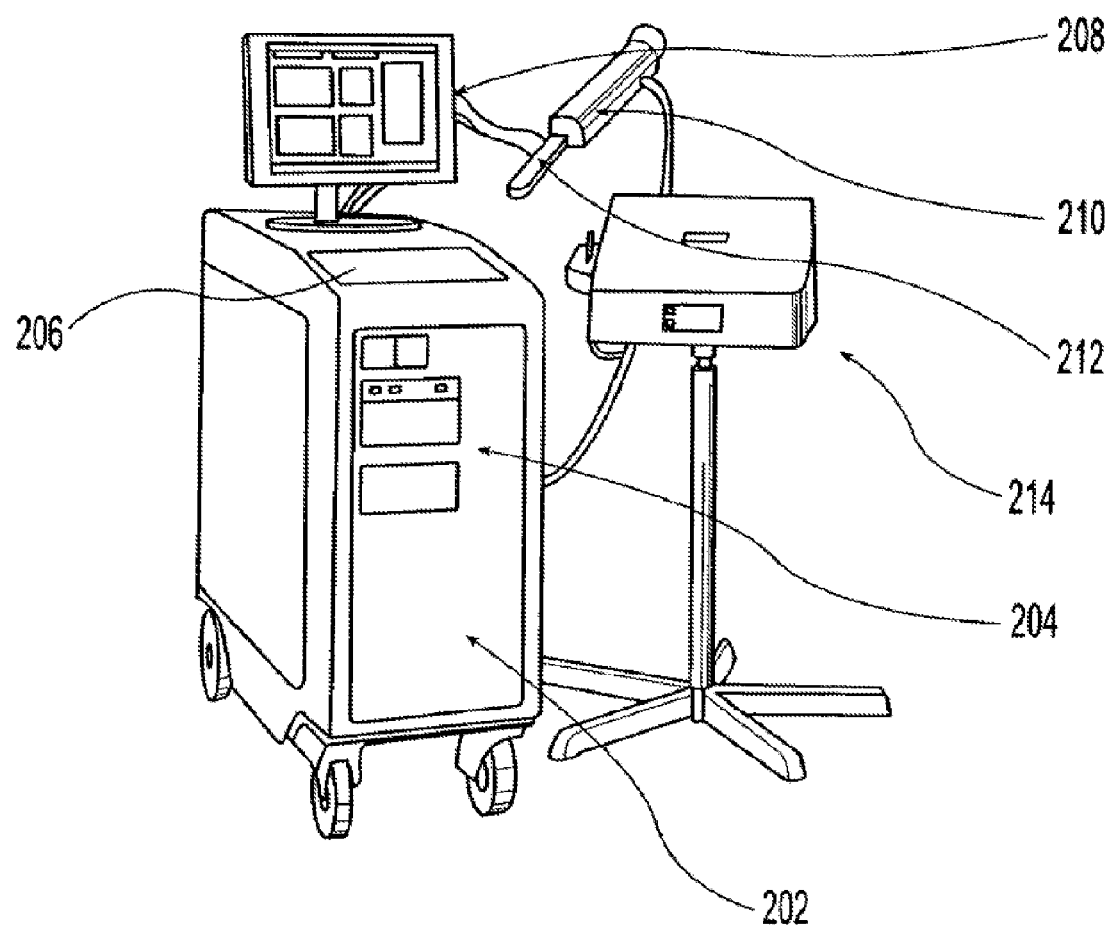
FIG. 2 is an exemplary embodiment of the HIFU System of FIG. 1.

Referring to FIG. 2, an exemplary HIFU System 200 is shown, the Sonablate® 500 HIFU System available from Focus Surgery, Inc., located at 3940 Pendleton Way, Indianapolis, Ind. 46226. HIFU System 200 includes a console 202 which houses or supports a controller (not shown), such as a processor and associated software; a printer 204 which provides hard copy images of tissue 10 and/or reports; a user input device 206 such as a keyboard, trackball, and/or mouse;

and a display 208 for displaying images of tissue 10 and software options to a user, such as a color display. Further, shown is a probe 210 which includes a transducer member (not shown), and a positioning member (not shown). Also shown is an articulated probe arm 212 which is coupled to console 202. Articulated probe arm 212 orients and supports probe 210. A chiller 214 is also shown. Chiller 214, in one embodiment, provides a water bath with a heat exchanger for the transducer member of probe 210 to actively remove heat from the transducer member during a HIFU Treatment.

Further details of suitable HIFU Systems which may be modified to execute the methods described herein are disclosed in U.S. Pat. No. 4,084,582; U.S. Pat. No. 4,207,901; U.S. Pat. No. 4,223,560; U.S. Pat. No. 4,227,417; U.S. Pat. No. 4,248,090; U.S. Pat. No. 4,257,271; U.S. Pat. No. 4,317,370; U.S. Pat. No. 4,325,381; U.S. Pat. No. 4,586,512; U.S. Pat. No. 4,620,546; U.S. Pat. No. 4,658,828; U.S. Pat. No. 4,664,121; U.S. Pat. No. 4,858,613; U.S. Pat. No. 4,951,653; U.S. Pat. No. 4,955,365; U.S. Pat. No. 5,036,855; U.S. Pat. No. 5,054,470; U.S. Pat. No. 5,080,102; U.S. Pat. No. 5,117,832; U.S. Pat. No. 5,149,319; U.S. Pat. No. 5,215,680; U.S. Pat. No. 5,219,401; U.S. Pat. No. 5,247,935; U.S. Pat. No. 5,295,484; U.S. Pat. No. 5,316,000; U.S. Pat. No. 5,391,197; U.S. Pat. No. 5,409,006; U.S. Pat. No. 5,443,069, U.S. Pat. No. 5,470,350, U.S. Pat. No. 5,492,126; U.S. Pat. No. 5,573,497, U.S. Pat. No. 5,601,526; U.S. Pat. No. 5,620,479; U.S. Pat. No. 5,630,837; U.S. Pat. No. 5,643,179; U.S. Pat. No. 5,676,692; U.S. Pat. No. 5,840,031; U.S. Pat. No. 5,762,066; U.S. Pat. No. 6,685,640; U.S. patent application Ser. No. 11/070,371, filed Mar. 2, 2005, titled "Ultrasound Phased Arrays,"; U.S. patent application Ser. No. 11/568,599, filed Nov. 2, 2006, U.S. patent application Ser. No. 11/177,827, filed Jul. 8, 2005; U.S. patent application Ser. No. 11/175,947, filed Jul. 6, 2005; and U.S. patent application Ser. No. 11/524,864, filed Sep. 21, 2006, the disclosures each of which is expressly incorporated herein by reference.

HIFU System 100 provides HIFU Therapy to tissue 10. The characteristics of the tissue 10 changes due to the HIFU Therapy. Some HIFU-induced lesions in tissue 10 are visually detectable changes through standard 2-D ultrasound (echo) imaging techniques (i.e. the HIFU-induced tissue change is sufficiently large enough to create a noticeable difference between a BEFORE and an AFTER HIFU image that the operator can see). In some situations, the application of HIFU may result in successful treatment of the tissue, even though these changes are not visually detectable through standard 2-D ultrasound (echo) imaging (i.e. cases wherein the tissue change due to HIFU is small or subtle enough so that it does not cause a noticeable change in standard ultrasound images). Disclosed herein are methods to detect tissue change referred to herein as tissue change monitoring methods ("TCM").

In one embodiment, TCM uses the same 2-D ultrasound echo data which is used for traditional ultrasound imaging. In traditional ultrasound imaging this ultrasound echo data is rectified, envelope-detected, log-scaled, and then mapped to a grayscale table for displaying on the screen. This processing removes the phase information from the ultrasound back scattered data and presents images based on intensity (square of pressure) values of the backscattered radio frequency signals. In one embodiment, TCM uses the phase information and the amplitude information of the ultrasound data to determine the changes introduced to the tissue due to exposure to HIFU Therapy.

In a first exemplary embodiment, the treatment region and surrounding tissue is imaged with HIFU System 100 using conventional ultrasound techniques. HIFU System 100 generates and stores a plurality of 2-D images of tissue 10 including treatment region 12. In one example, HIFU System 100 generates and stores a plurality of transverse or sector images about every 3 mm along the treatment region, such as image 121 in FIG. 15, and generates and stores a plurality of sagittal (or linear) images about every 3° (as represented by image planes 250 in FIG. 5), such as image 123 in FIG. 15. The sagittal images are comprised of a plurality of one-dimensional radio frequency echoes 252 (see FIG. 6) which each represent a line in the sagittal images. In one embodiment, about 200 to about 250 one-dimensional radio frequency echoes are included in the sagittal image with each one-dimensional radio frequency echo being spaced about 0.2 millimeters from adjacent one-dimensional radio frequency echoes. Each one-dimensional radio frequency echo is acquired at a corresponding transducer position along the x-axis 114. In other examples, different spacing of the transverse and sagittal images are used.

As used herein, the term "treatment region" is defined as one or more portions of tissue which are to be treated during a HIFU Treatment. In general, treatment region is used to describe the overall area being treated during a HIFU Treatment. However, treatment region may also be used to describe one or more sub-regions of the overall area being treated, such as one or more treatment segment(s) and/or one or more treatment site(s).

TCM provides a method for detecting changes in the tissue being treated with HIFU Therapy even if the HIFU Therapy does not result in large lesions that produce very large backscattered signals. In one embodiment, TCM is the process of acquiring ultrasound backscattered RF echo data prior to, during, and/or after the delivery of HIFU Therapy, processing this data to determine a level of tissue change, assigning a visual indicia to the level of tissue change, and superimposing the visual indicia on an image of the treatment region. Exemplary images include standard 2D ultrasound images (such as images 121 and 123 in FIG. 15) and volumetric ultrasound images, such as image 125 in FIG. 17. Image 125 includes a three-dimensional representation of the backscatter echo data, the visual indicator of the tissue change, and a representation of the position of the transducer 104.

Figure 3:
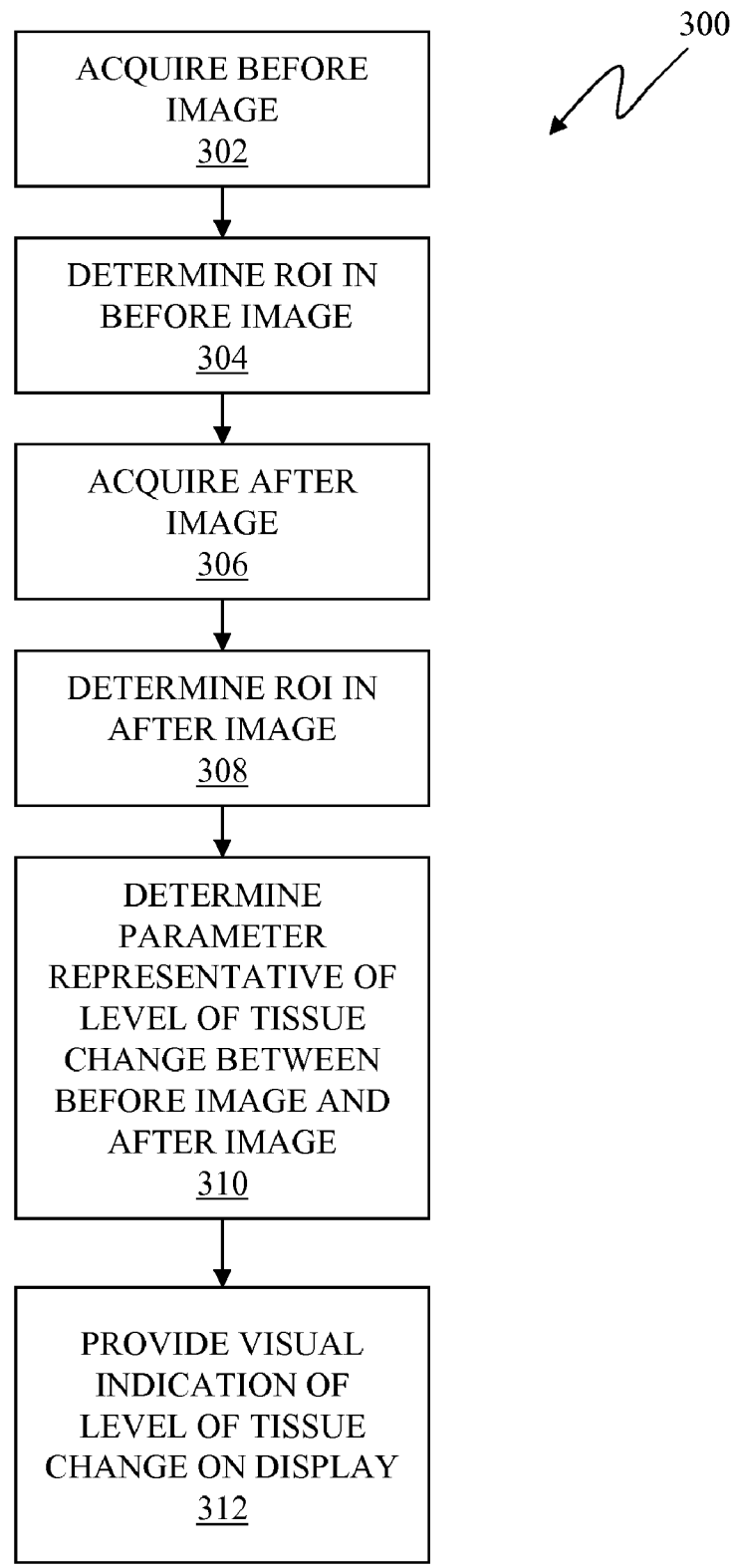
FIG. 3 is an exemplary method for treating tissue.

Referring to FIG. 3, an exemplary embodiment 300 of a TCM is shown. Prior to delivering HIFU Therapy to create tissue changes, the HIFU System 100 acquires a reference image which includes the region that will be treated by the HIFU Therapy, as represented by block 302. This image is referred to as a BEFORE image. The BEFORE image may be acquired just prior to the application of HIFU Therapy or may be acquired many seconds prior to the application of HIFU Therapy. In the illustrated embodiment, the BEFORE image is a sagittal image comprised of a plurality of one-dimensional echo signals.

A region of interest (ROI) is identified in the image, as represented by block 304. The ROI is a 2D sub-region which contains echoes of the tissue volume that will be treated by the HIFU transducer in a subsequent HIFU Treatment. In one embodiment, the ROI includes the tissue located in the focal zone of the transducer (such as ROI 260 in FIG. 6). In one embodiment, the ROI includes the tissue located in the region between the transducer and the focal zone of the transducer (such as ROI 262 in FIG. 6). In one embodiment, the ROI includes the tissue located in the region beyond the focal zone of the transducer (such as ROI 264 in FIG. 6). In one embodiment, the ROI includes the tissue located between the transducer and the focal zone of the transducer, located in the focal zone of the transducer, and located in the region beyond the focal zone of the transducer. In the illustrated embodiment, the ROI is approximately from 10 millimeters to about 15 millimeters in depth and about 3 millimeters wide which corresponds to about 15 adjacent one-dimensional echo lines 252 in FIG. 6. The RF data contained in the ROI is one of the two input data sets used to determine the tissue change value caused by an exposure to HIFU Therapy.

The second input data set is the RF data from the ROI acquired subsequent to a HIFU exposure. An image is acquired after the HIFU exposure, as represented by block 306. This is referred to as an AFTER image. The same ROI is identified in the AFTER image, as represented by block 308. A parameter value representative of the tissue change is determined based on the BEFORE image and the AFTER image, as represented by block 310. In one embodiment, this parameter value is a level that is based on the tissue change value.

Figure 7:
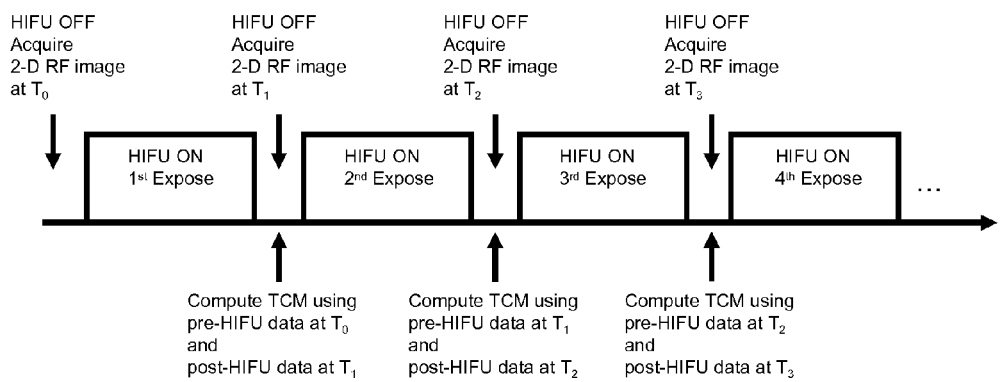
FIG. 7 represents a first exemplary method for the acquisition of 2D RF Data during a HIFU Treatment.

Referring to FIG. 7, an exemplary timeline for a portion of a HIFU Treatment is shown. A first BEFORE image is acquired at time $T_0$. A first HIFU Therapy is provided between time $T_0$ and time $T_1$. A first AFTER image is acquired at time $T_1$. A parameter value representative of the amount of tissue change during the first HIFU Therapy is determined. The first AFTER image is then used as a second BEFORE image. A second HIFU Therapy is provided between time $T_1$ and time $T_2$. A second AFTER image is acquired at time $T_2$. A parameter value representative of the amount of tissue change during the second HIFU Therapy is determined. The second AFTER image is then used as a third BEFORE image and the process continues to repeat.

Figure 8:
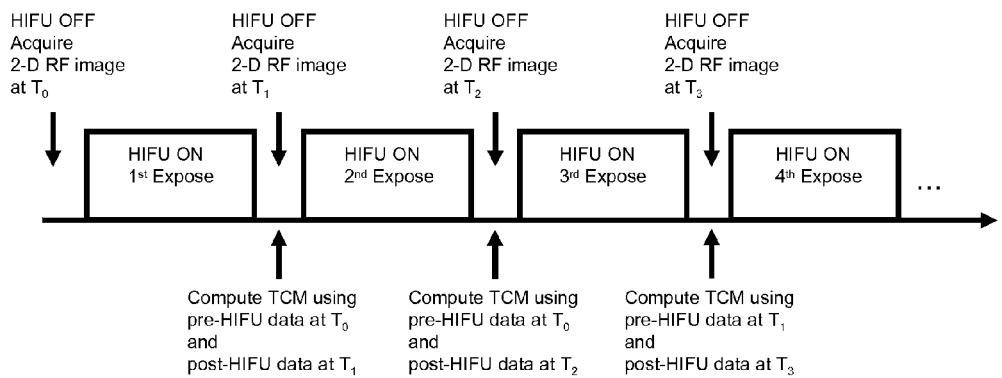
FIG. 8 represents a second exemplary method for the acquisition of 2D RF Data during a HIFU Treatment.

Referring to FIG. 8, another exemplary timeline for a portion of a HIFU Treatment is shown. A first BEFORE image is acquired at time $T_0$. A first HIFU Therapy is provided between time $T_0$ and time $T_1$. A first AFTER image is acquired at time $T_1$. A parameter value representative of the amount of tissue change during the first HIFU Therapy is determined. A second HIFU Therapy is provided between time $T_1$ and time $T_2$. A second AFTER image is acquired at time $T_2$. A parameter value representative of the amount of tissue change during the first HIFU Therapy and the second HIFU Therapy is determined. The first AFTER image is then used as a second BEFORE image. A third HIFU Therapy is provided between time $T_2$ and time $T_3$. A third AFTER image is acquired at time $T_3$. A parameter value representative of the amount of tissue change during the second HIFU Therapy and the third HIFU Therapy is determined. The second AFTER image is then used as a third BEFORE image and the process continues to repeat.

The situation shown in FIG. 8 is beneficial in situations wherein successive treatment sites are in close proximity, such as next to each other. In this situation, the HIFU Therapy for an $n^{th}$ treatment site may likely cause a tissue change in the adjacent n+1 treatment site due to heat conduction. As such, if the image recorded after the exposure of the nth treatment site is used as the BEFORE image of the n+1 treatment then a portion of the tissue change at the n+1 treatment site is not taken into account (the portion corresponding to the nth exposure). By using the BEFORE image prior to the nth exposure as the BEFORE image for the n+1 exposure the overall tissue change to the n+1 treatment site due to the nth exposure and the n+1 exposure may be determined.

Once the BEFORE image and the AFTER image of the ROI are acquired, the parameter value representative of the level of tissue change is determined. A power spectrum is determined for each of the one dimensional echoes of the ROI for each of the BEFORE image and the AFTER image. At this point two two-dimensional power spectra are known. One corresponding to the BEFORE image ROI and one corresponding to the AFTER image ROI. An average power spectrum for each of the BEFORE image ROI and the AFTER image ROI are determined. At this point two one-dimensional power spectra are known. One corresponding to the BEFORE image and one corresponding to the AFTER image.

For each of the two averaged power spectra, the energy level of a plurality of frequency bands is determined. In the illustrated embodiment shown in FIG. 9, three frequency bands 272, 274, and 276 are determined for the averaged power spectrum 270 of the AFTER image. The same frequency bands are used in the averaged power spectrum of the BEFORE image. At this point, for each of the BEFORE image and the AFTER image three characteristics are known, the energy levels for each of frequency bands 272, 274, and 276.

The determined energy level difference between the BEFORE image and the AFTER image is determined for each frequency band. The largest of the determined differences, in one embodiment, is the parameter value representative of the level of tissue change between the BEFORE image and the AFTER image. The largest of the determined differences is mapped to a level of tissue change. A visual indicia indicative of the level of tissue change is displayed on the display 112 of HIFU System 100, as represented by block 312. In one embodiment, the visual indicia is a color. The following table illustrates an exemplary mapping of the difference value to a visual indicator, a color, for a piece of chicken test tissue having an initial temperature of about 30 to about 35 degrees Celsius (C.).

| Normalized TCM Readings | Color | Measured Peak Temperature (C.) | $\Delta T$ (C.) (peak T-initial T) | Increase in the Average Power Spectrum |
|---|---|---|---|---|
| <0.33 | green | 48 | <18 | <3.3 dB |
| 0.33-0.66 | yellow | 65 | 19-35 | 3.3-6.6 dB |
| >0.66 | orange | 90 | 36-60 | >6.6 dB |

Figure 15:
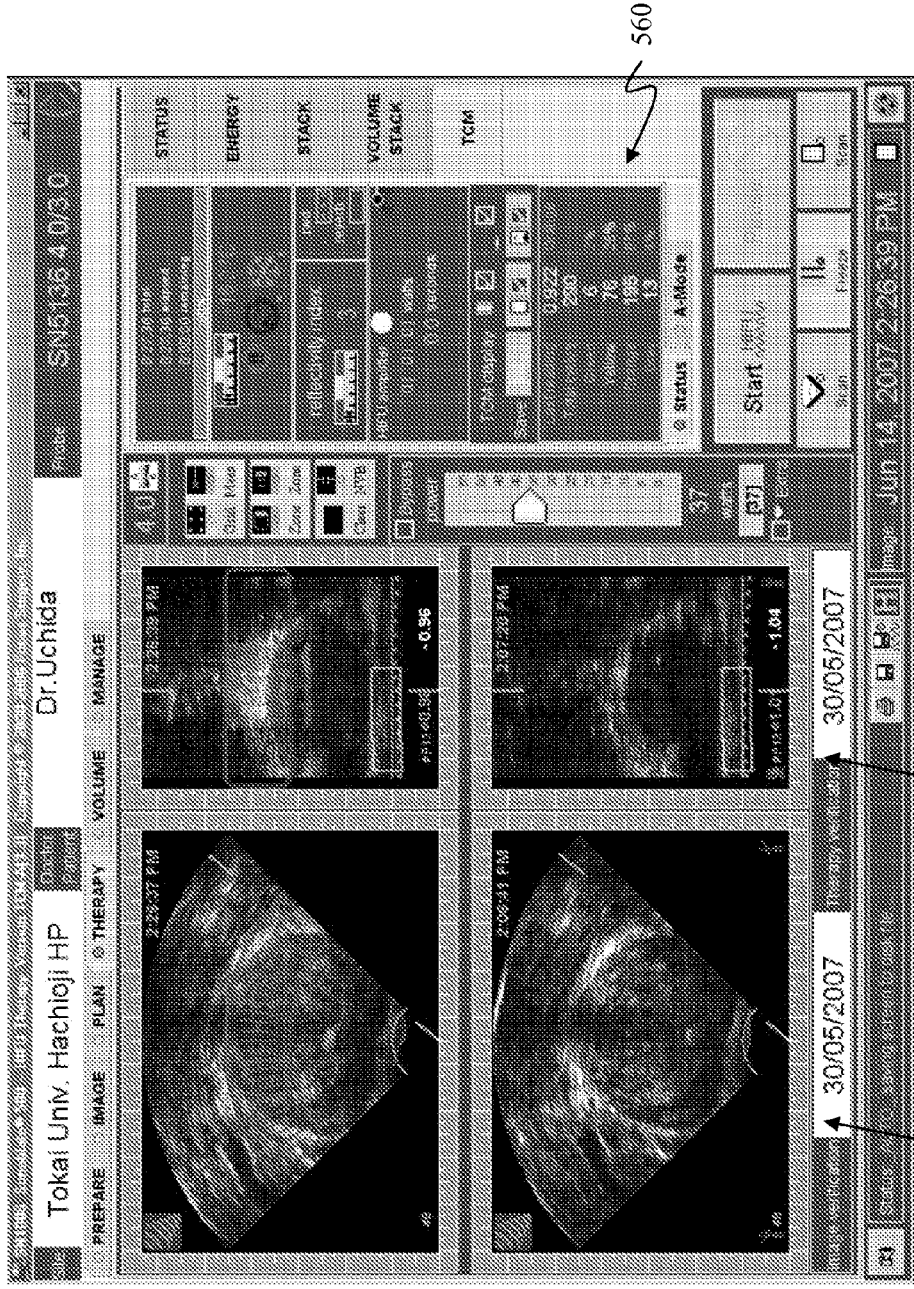
FIG. 15 is an exemplary screen shot of the display of the HIFU System of FIG. 1 illustrating an image of the prostate including visual indicators of the tissue change and a summary of the TCM.

In one embodiment, the color is overlaid onto a displayed ultrasound image, such as image 123 in FIG. 15, in a region corresponding to the treatment site in the ROI. This process is repeated for each successive BEFORE image and AFTER image.

Figure 4:
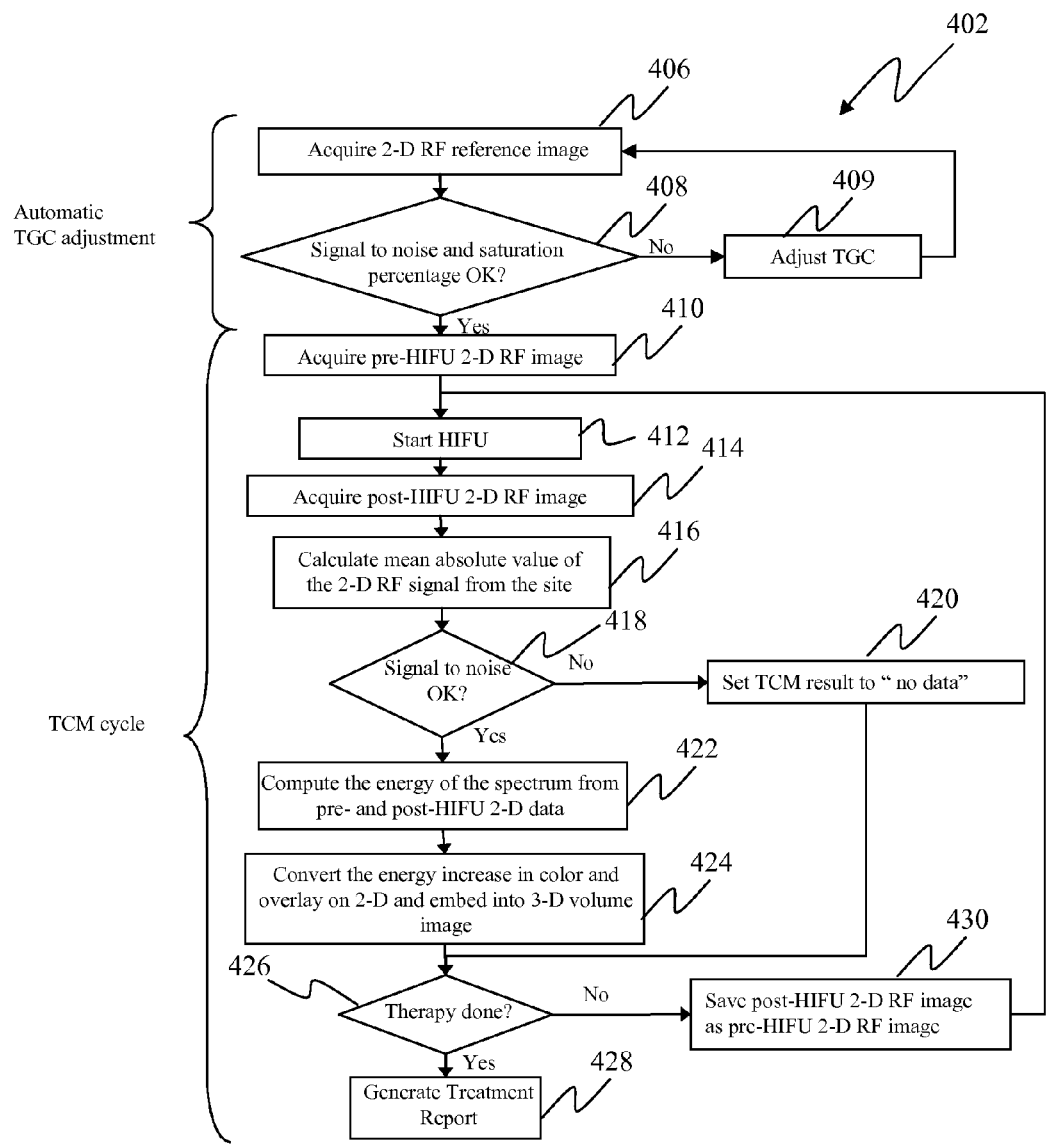
FIG. 4 is an exemplary method for treating tissue.

Referring to FIG. 4, an exemplary implementation of a TCM method 400 is disclosed. HIFU System 100 performs a diagnostic mode of operation 402 and a treatment mode of operation 404. HIFU System 100 further performs an imaging mode of operation in which images of treatment region 12 are acquired.

During the diagnostic mode of operation 402, a two dimensional reference image is acquired as represented by block 406. During ultrasound imaging a pulse is sent into the tissue and the echoes from that pulse are digitized and converted into an image. As the sound travels into the tissue and the echoes return, the time for a given echo is directly proportional to the depth of the echo source. As the ultrasound travels through tissue, its intensity reduces the further it travels. A gain parameter is applied to compensate for this physical phenomenon by generally increasing the gain for deeper tissue echoes. The gain parameter is generally known as either TGC which is an acronym for Time Gain Control or DGC which is an acronym for Depth Gain Control.

The image is analyzed to determine if the signal to noise level is sufficient for TCM, as represented by block 408. In one embodiment, the RF signals of the ultrasound image which correspond to a region of interest is examined. The mean of the absolute values of the RF signal is determined.

The percentage of data points in the RF signal that are saturated is determined. A data point is saturated if its value exceeds or is equal to the maximum value that the analog to digital converter is able to digitize. If the mean value of the RF signal is below a threshold then the gain parameter is increased (as represented by block 409) and another ultrasound image is taken and the RF signal is tested once again. This approach helps prevent false positive readings due to poor signal to noise level from cysts (dark areas) in the tissue. An exemplary mean value threshold is about 10% of maximum digitization value. If the percent of saturated data points is above a threshold, then the gain parameter is decreased and another ultrasound image is taken and the RF signal is tested once again. This approach helps prevent false negative readings from excessively large signals caused by high gain in settings in the ultrasound image (saturation). An exemplary threshold percentage is about 0.1 percent. Assuming that both the mean value and the saturation percentage satisfy their respective thresholds, a HIFU Therapy including tissue change monitoring may be performed. If one or both of the mean value and the saturation percentage do not satisfy their respective thresholds, then a HIFU Therapy may still be performed. TCM may still be on in each HIFU treatment sites except where the mean value does not satisfy the threshold.

Figure 14:
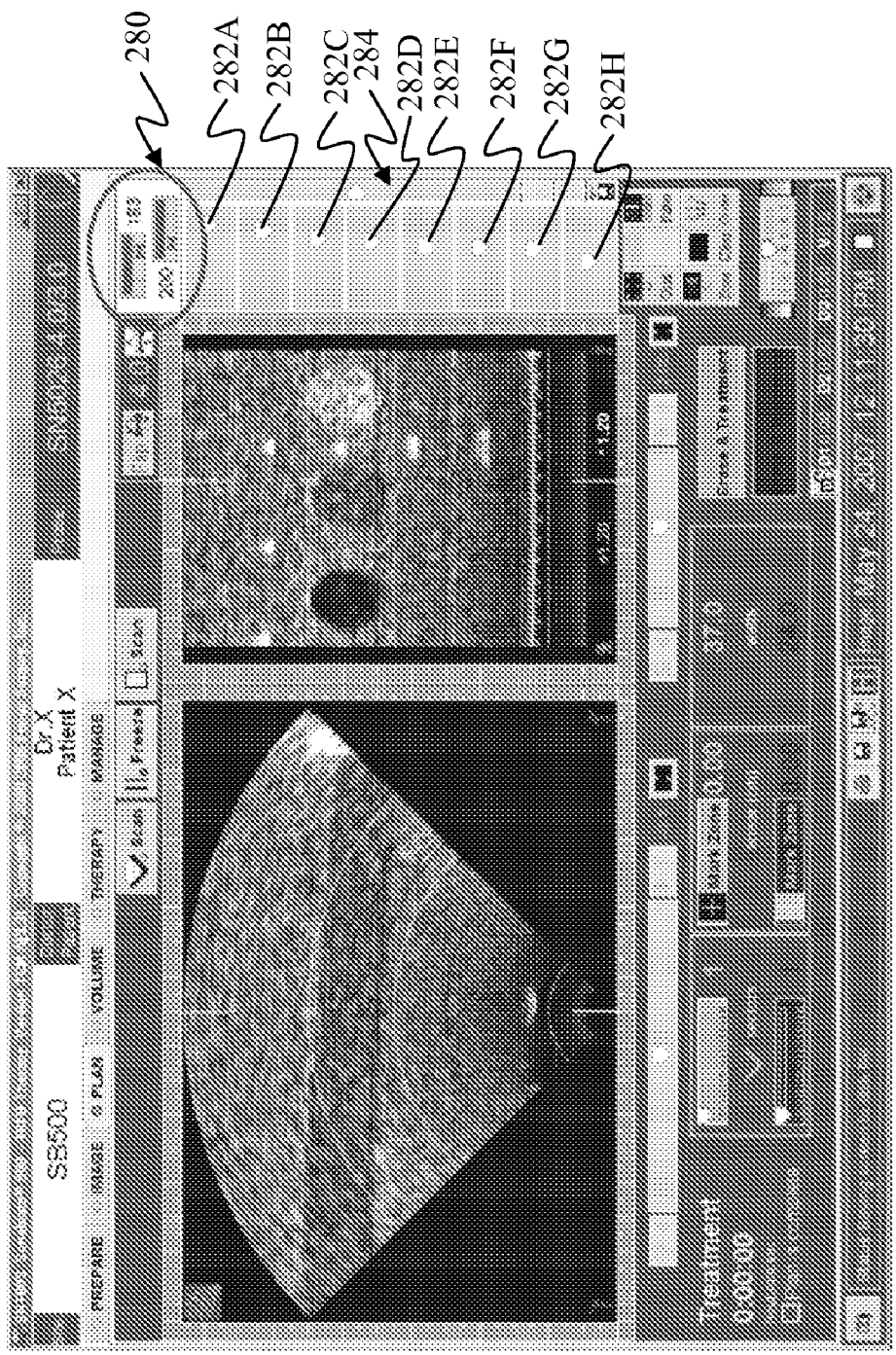
FIG. 14 is an exemplary screen shot of the display of the HIFU System of FIG. 1 illustrating inputs for modifying the gain parameters during a diagnostic mode of operation.

In one embodiment, both a signal to noise level and a RF saturation level are determined and presented with a scale meter 280 (see FIG. 14) on the display 112 of HIFU System 100. The operator may make fine adjustments for a gain parameter with input controls 282A-H in FIG. 14 and a main gain with input control 284 in FIG. 14. The gain parameters corresponding to input controls 282A-H each correspond to a given depth range. As such, the gain for various depths may be adjusted independently. The main gain input 284 adjusts the gain for all depths at the same time.

A BEFORE image is acquired for a treatment region, as represented by block 410. In one embodiment, the BEFORE image is a two-dimensional image, such as a sagittal image, that includes the plane of the upcoming HIFU exposure (i.e. a plane containing the focal point of the transducer). The BEFORE image is stored in memory.

HIFU Therapy is applied to the tissue as represented by block 412. Once the tissue has been exposed to the HIFU Therapy, an AFTER image is acquired for the treatment region, as represented by block 414. The AFTER image, like the BEFORE image, in one embodiment is a two-dimensional image that includes the plane in which the HIFU Therapy was directed. The AFTER image is stored in memory.

The BEFORE image is examined to determine whether the signal has a sufficient signal to noise ratio to be analyzed for tissue change monitoring, as represented by blocks 416 and 418. In the illustrated embodiment, the mean of the absolute values of RF data in the treatment region in the BEFORE image is determined. If the mean value is below a threshold, then the BEFORE image is not considered appropriate for analyzing for tissue change monitoring and a tissue change indicator is set to "no data", as represented by block 420. In one embodiment, the indicator is a visual indicator on the display of HIFU System 100. If the mean value satisfies the threshold, then the amount of tissue change is determined, as represented by block 422. An exemplary method for determining the amount of tissue change is provided in FIG. 10 discussed herein.

Figure 10:
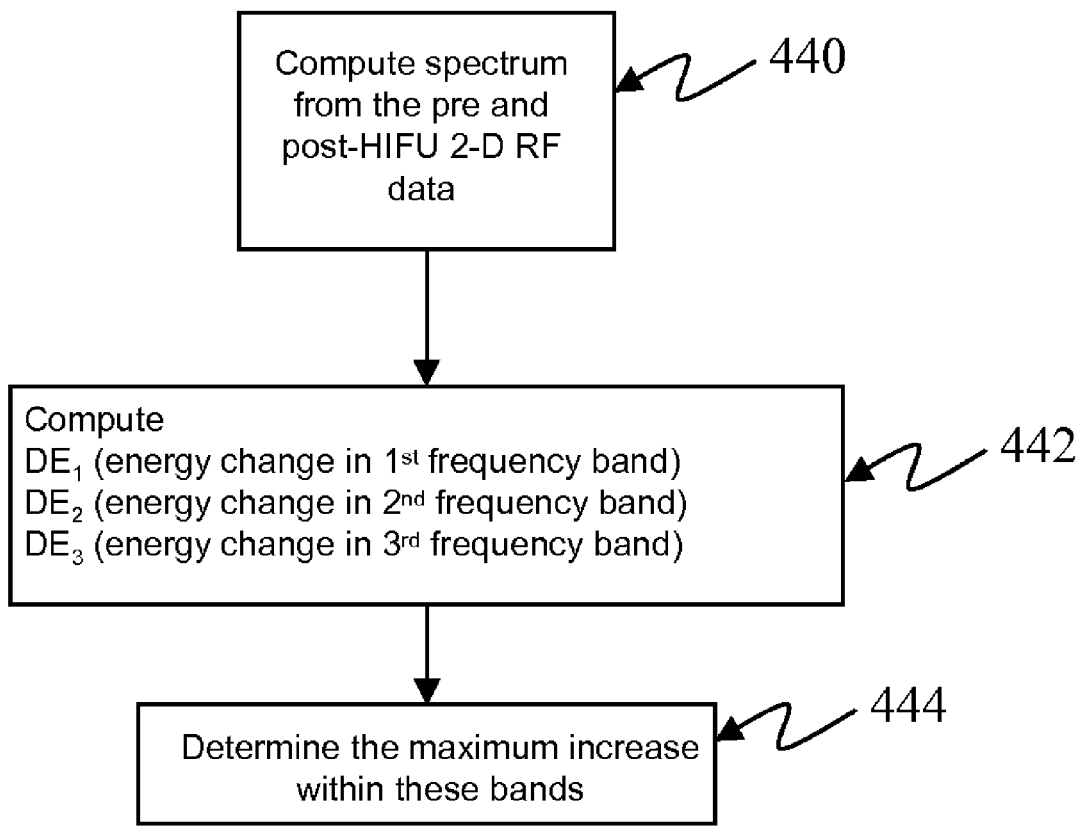
FIG. 10 is an exemplary method for determining a tissue change value.

As discussed in relation to FIG. 10, a parameter value is determined which provides an indication of the level of tissue change. In the illustrated embodiment, the parameter is an energy increase. The parameter is mapped to a visual indicator and displayed on display of HIFU System 100, as represented by block 424. In the illustrated embodiment, the visual indicator is a color and the visual indicator is overlaid on a two-dimensional image of the treatment region and embedded into a three-dimensional volume image. In one embodiment, discrete colors are provided which correspond to discrete levels of energy increase. In one embodiment, a green color code corresponds to no (or very small) tissue change, a yellow color code corresponds to a moderate tissue change, and an orange corresponds to a large tissue change.

A check is made to determine if a HIFU Treatment is complete, as represented by block 426. If the HIFU Treatment is complete then a treatment report is generated, as represented by block 428. If the HIFU Treatment is not complete then the AFTER image is designated as the BEFORE image for the next treatment site (assuming that the next treatment site is in the same plane and not adjacent the last treatment site wherein the process in FIG. 8 is used), as represented by block 430. If the next treatment site is in a different plane, a new BEFORE image is acquired.

Figure 5:
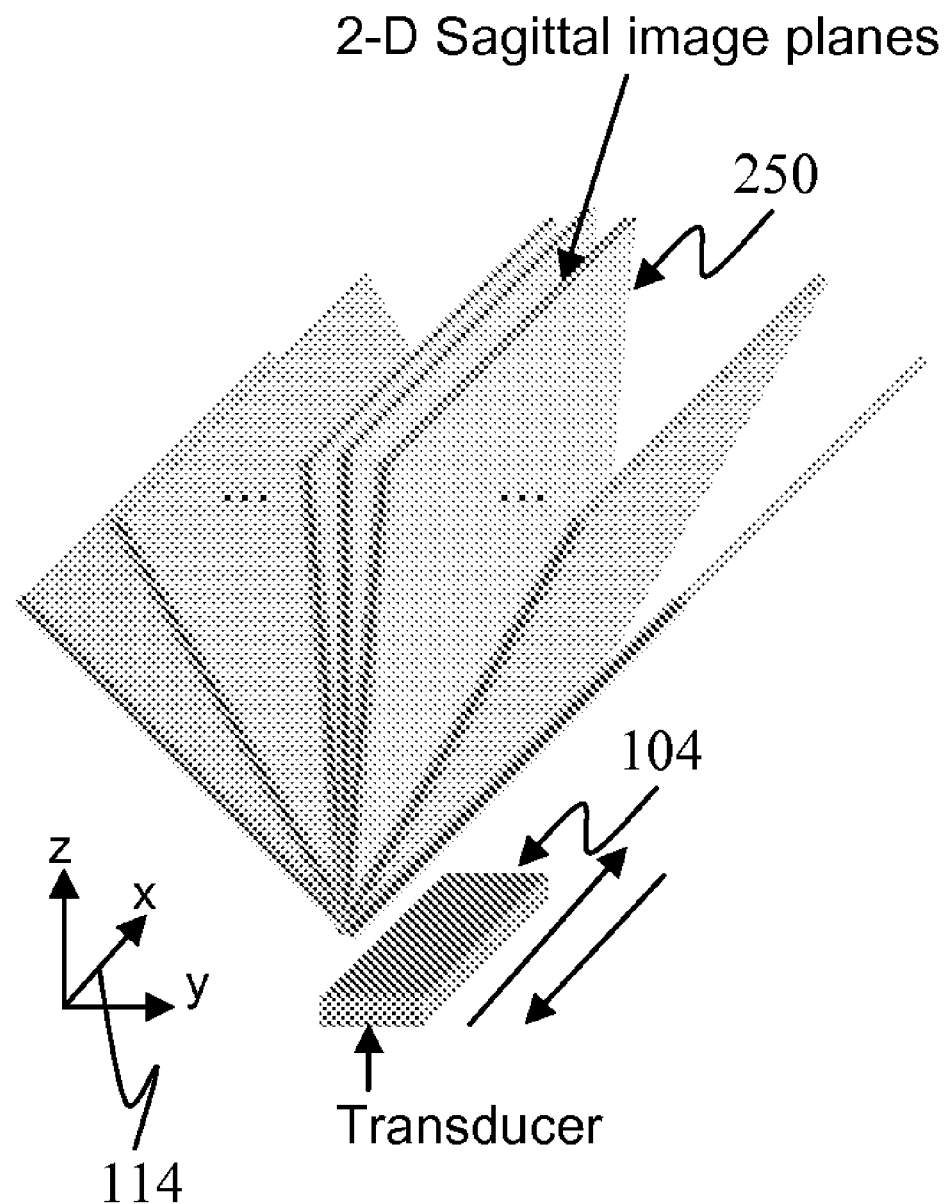
FIG. 5 represents exemplary sagittal image planes.

In the determination of the parameter value of the tissue change, one or more regions of interest are determined. Referring to FIG. 5, an exemplary BEFORE image and an exemplary AFTER image are both in a plane 250 and are acquired by translating transducer in the x-direction 114. At each discrete location in the x-direction 114 a one dimensional echo signal 252 is recorded. An exemplary spacing of the discrete locations is about 0.2 millimeters.

Figure 6:
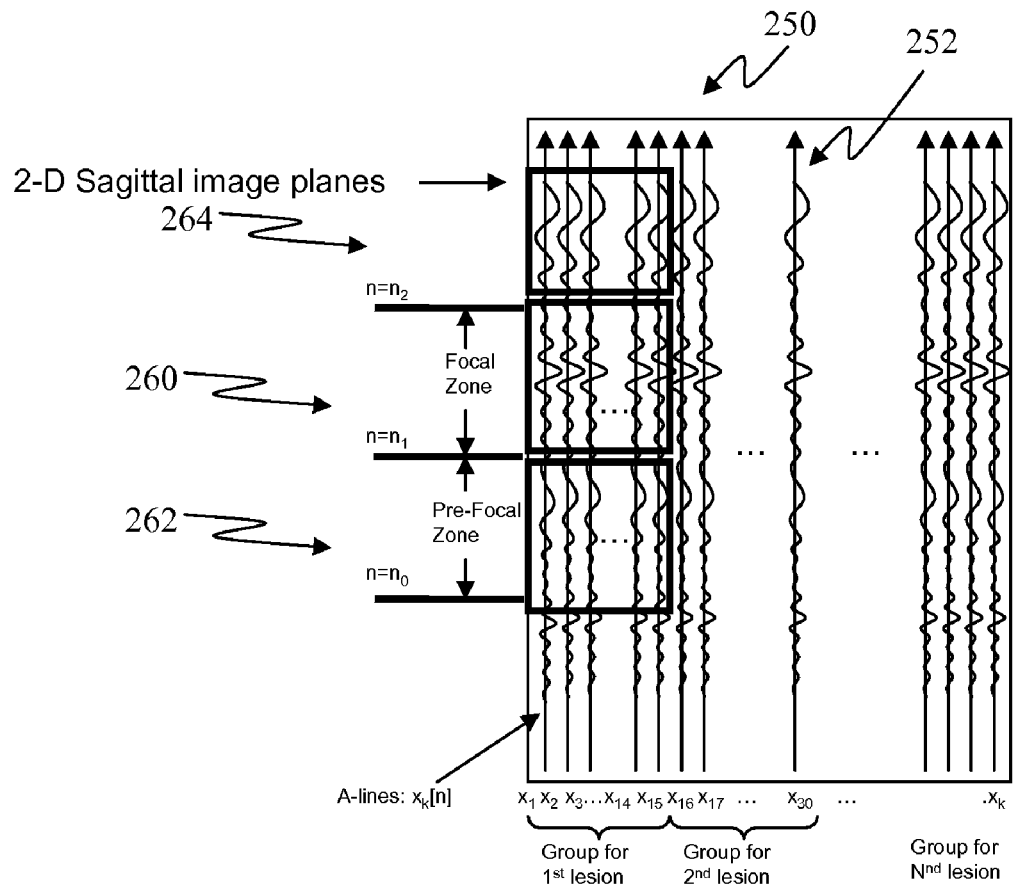
FIG. 6 represents exemplary echo signals received for a given sagittal image plane.

A plurality of one-dimensional echo signals 252 are shown in FIG. 6. In one embodiment, about 200 to about 250 one-dimensional echo lines 252 are included in each of the BEFORE image an the AFTER image. In one embodiment, about 225 one-dimensional echo lines 252 are included in each of the BEFORE image and the AFTER image.

In one embodiment, a width of a region of interest is comprised of a discrete number of one-dimensional echo lines 252. An exemplary width is about 15 one-dimensional echo lines 252 at a spacing of about 0.2 millimeters. This width is associated with a first treatment site. The fifteen adjacent one-dimensional echo lines 252 are associated with a second treatment site, although not necessarily second in time.

As shown in FIG. 6, two regions of interest are monitored for the first treatment site (and for successive treatment sites thereafter). A first region of interest 260 corresponds to the focal zone. In one example, the first region corresponds to a depth of about 3.5 cm to about 4.5 cm. A second region of interest 262 corresponds to a pre-focal region. In one example, the second region of interest corresponds to a depth of about 2.8 cm to about 3.5 cm. By monitoring the tissue change in the pre-focal region of interest an early detection of pre-focal heating may be determined. By avoiding pre-focal heating the therapy safety is improved and the therapy time is shortened. Further, the detection of pre-focal heating may be able to save therapy time by optimizing the radial overlap of consecutive therapy zones. In one embodiment, a third region of interest 264 corresponding to the region beyond the focal zone (beyond the first region of interest) is also monitored. Additional regions of interest such as for other treatment sites may also be monitored.

Referring to FIG. 10, the parameter corresponding to the tissue change in a given region of interest is determined. The power spectrum for the region of interest for each of the BEFORE image and the AFTER image is determined, as represented by block 440. The time domain echoes signals for each one-dimensional echo line in the region of interest are converted to the frequency domain for the depth range corresponding to the region of interest for both the BEFORE image and the AFTER image. In one embodiment, a discrete Fourier transform is used to convert the respective signals to the frequency domain. The converted signals are then averaged for each of the BEFORE image and the AFTER image to form a single power spectrum for each of the BEFORE image and the AFTER image. It should be noted if multiple regions of interest are being monitored then power spectra for those regions of interest in the BEFORE image and the AFTER image are also determined.

Figure 9:
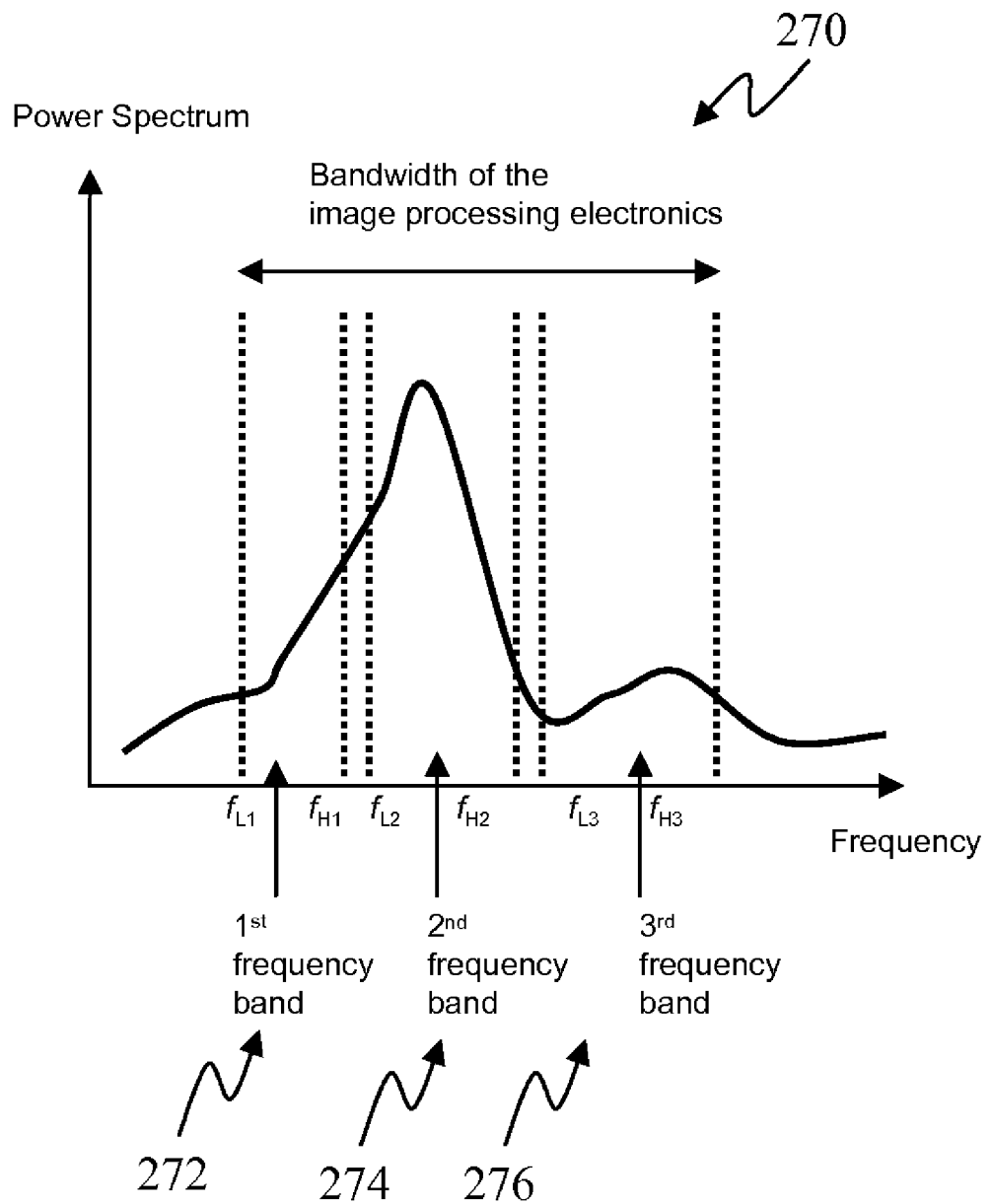
FIG. 9 represents exemplary frequency bands of an exemplary power spectrum.

An exemplary power spectrum 270 is illustrated in FIG. 9 for a region of interest corresponding to the focal zone of the transducer at a given treatment site. A plurality of frequency bands 272, 274, 276 are indicated on the power spectrum. The frequency bands correspond to a fundamental frequency band 274, a sub-harmonic frequency band 272, and a harmonic frequency band 276 by way of example. In one embodiment, for a fundamental transducer operating frequency of 4 MHz, the fundamental frequency band correspond to the bandwidth of about 3 megahertz (MHZ) to about 5 MHz, the sub-harmonic frequency band corresponds to a bandwidth of about 1 MHz to about 3 MHz, and the harmonic frequency band corresponds to the bandwidth of about 6 MHz to about 9 MHz.

The change in energy in each of the frequency bands 272, 274, 276 between the BEFORE image and the AFTER image is determined, as represented by block 442. In one embodiment, the average power spectrum for each frequency band in both of the BEFORE image and the AFTER image are determined. The power spectrum for each echo line ($k^{th}$ line) is determined by equation 1

$$P_k(f) = \left|\sum_{n=n_1}^{n_2} x_k[n] e^{-j \cdot 2\pi f \cdot \frac{(n-n_1)}{(n_2-n_1)}}\right|^2 \tag{1}$$

wherein $P_k(f)$ is the power spectrum from the focal zone data in the $k^{th}$ echo line, $x_k[n]$ is digitized RF data in the focal zoon at the $k^{th}$ echo line location, and the focal zone range is from depth $n_1$ to depth $n_2$. The average power spectrum across a plurality of echo lines is determined by equation 2 wherein it is assumed that 15 echo lines are being averaged. Referring to equation 2

$$P_{avg}(f) = \frac{1}{15} \sum_{k=1}^{15} P_k(f) \tag{2}$$

wherein $P_{avg}(f)$ is the average power spectrum, 15 is the number of echo lines.

Next the average power spectrum in dB scale is determined for each frequency band. The average power spectrum for the sub-harmonic band 272 is determined by equation 3

$$E_{SH} = 10 \cdot \log_{10}\left(\frac{1}{(f_{H1} - f_{L1})} \sum_{f_{L1}}^{f_{H1}} P_{avg}(f)\right), \tag{3}$$

wherein $E_{SH}$ is the average of power spectrum in dB scale in the sub-harmonic band, $P_{avg}(f)$ is the average power spectrum, $f_{L1}$ is the lower frequency boundary of the sub-harmonic band 272 and $f_{H1}$ is the upper frequency boundary of the sub-harmonic band. The average power spectrum for the fundamental band 274 is determined by equation 4

$$E_F = 10 \cdot \log_{10}\left(\frac{1}{(f_{H2} - f_{L2})} \sum_{f_{L2}}^{f_{H2}} P_{avg}(f)\right), \tag{4}$$

wherein $E_F$ is the average of power spectrum in dB scale in the fundamental band, $P_{avg}(f)$ is the average power spectrum, $f_{L2}$ is the lower frequency boundary of the fundamental band and $f_{H2}$ is the upper frequency boundary of the fundamental band 274.

The average power spectrum for the harmonic band 276 is determined by equation 5

$$E_H = 10 \cdot \log_{10}\left(\frac{1}{(f_{H3} - f_{L3})} \sum_{f_{L3}}^{f_{H3}} P_{avg}(f)\right), \tag{5}$$

wherein $E_H$ is the average of power spectrum in dB scale in the harmonic band, $P_{avg}(f)$ is the average power spectrum, $f_{L3}$ is the lower frequency boundary of the harmonic band 276 and $f_{H3}$ is the upper frequency boundary of the harmonic band.

The average power spectrums ($E_{SH}$, $E_F$, and $E_H$) are determined for each of the BEFORE image and the AFTER image. The differences in each of the average power spectrums ($E_{SH}$, $E_F$, and $E_H$) for each frequency band are then determined as represented in equations 6-8.

$$\Delta E_{SH} = E_{SH}(T_1) - E_{SH}(T_0) \tag{6}$$

$$\Delta E_F = E_F(T_1) - E_F(T_0) \tag{7}$$

$$\Delta E_H = E_H(T_1) - E_H(T_0) \tag{8}$$

The maximum of $\Delta E_{SH}$, $\Delta E_F$, and $\Delta E_H$ is then determined, as represented by block 444. It is this energy difference (increase) that corresponds to the value of the tissue change and which is converted to a corresponding visual indicator in block 424 in FIG. 4.

Figure 11:
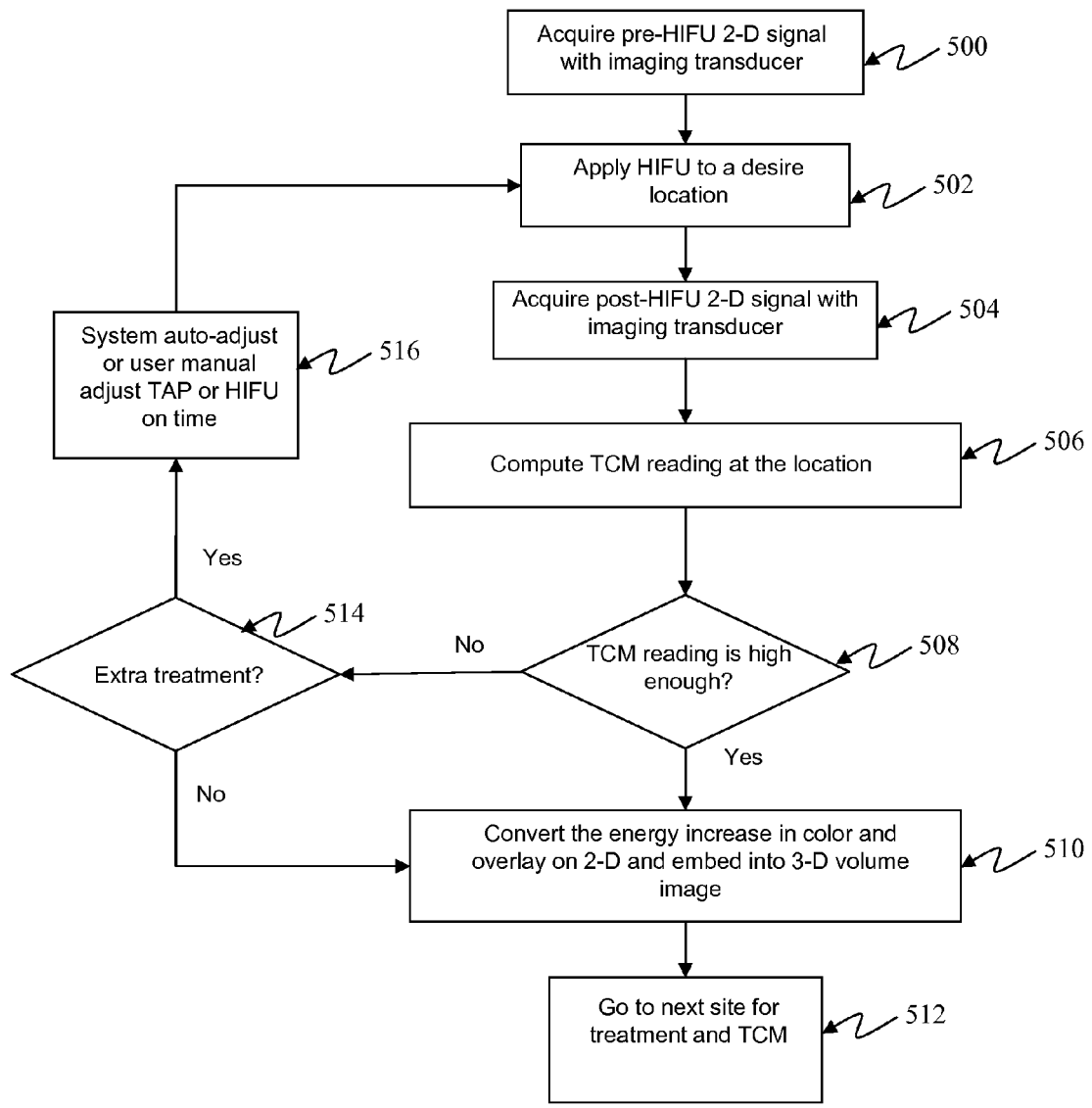
FIG. 11 is an exemplary method for determining if an additional treatment is to be performed at a given treatment site.

Referring to FIG. 11, the tissue change monitoring is applied to decision making during a HIFU Treatment. These decisions may be made by a surgeon based on the visual indications of the tissue change provided on the display 112 of HIFU System 100. In one embodiment, these decisions are made in the software 109 of HIFU System 100.

A BEFORE image is acquired for a given treatment site, as represented by block 500. HIFU Therapy is applied to the treatment site, as represented by block 502. In one embodiment, a pause of about 0.5 seconds is inserted after the application of HIFU Therapy to the treatment site. An AFTER image is acquired for the treatment site, as represented by block 504. The tissue change parameter value is determined for one or more regions of interest, as represented by block 506. The tissue change parameter value is compared to a threshold tissue change value, as represented by block 508.

If the tissue change parameter value satisfies the threshold tissue change value, then the tissue change parameter value is mapped to a visual indication which is displayed on the display of HIFU System 100, as represented by block 510. The transducer is then moved to the next treatment location in a treatment plan and the process is repeated for the new treatment site, as represented by block 512. If the tissue change parameter value does not satisfy the threshold tissue change value, a decision is made whether to perform an extra exposure at the treatment site, as represented by block 514. In one embodiment, the operator of HIFU System 100 determines whether to perform an additional exposure or not. In one embodiment, the HIFU System 100 determines whether to perform an additional exposure based on the level of detected tissue change and/or the physician's judgement. If an additional exposure is to be performed, the parameters of the exposure are determined as represented by block 516. In one embodiment, the total acoustic power (TAP) and/or HIFU on time (length of HIFU Therapy) are adjusted.

In one embodiment, the tissue change parameter value from a previous treatment site is used to determine the HIFU exposure variables for a current treatment site. The tissue change parameter value may correspond to a focal zone region of interest. The tissue change parameters value may correspond to a pre-focal zone region of interest. In one embodiment, both a tissue change parameter value for a focal zone region of interest and a tissue change parameter value for pre-focal zone region of interest are monitored to determine the variable for a current treatment site.

Figure 12:
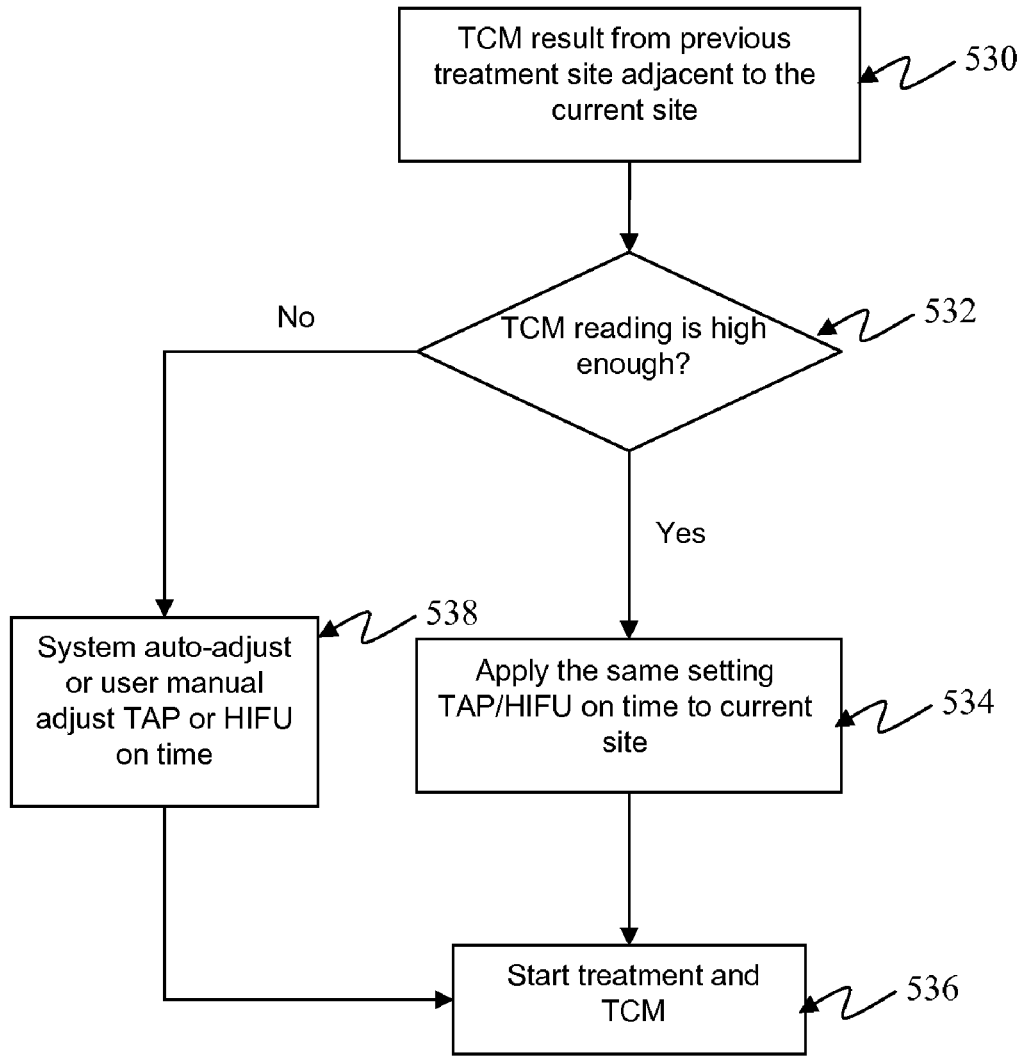
FIG. 12 is an exemplary method to determine the parameters for a current treatment site based on the tissue change at a prior treatment site.

Referring to FIG. 12, the tissue change parameter value(s) from a previous treatment site adjacent a current treatment site is determined, as represented by block 530. The tissue change parameter value(s) is compared to a tissue change threshold to determine if the tissue change parameter values are acceptable, as represented by block 532. In the case of the focal zone region of interest, the tissue change parameter value is checked to see if it is at or above the threshold value. If the tissue change value is low, the total acoustic power and/or the duration of the HIFU exposure for the current treatment site may be increased. In the case of a pre-focal zone region of interest, the tissue change parameter value is checked to see if it is below a threshold value. If the tissue change value is above the threshold amount, microbubbles may have formed in the pre-focal regions. These microbubbles attenuate the HIFU Therapy that is to be delivered to the treatment site. As such, if the tissue change value is above the threshold amount, then the total acoustic power for the current treatment site may be reduced and/or the amount of off time before the commencement of the treatment of the current treatment site is increased.

If the tissue change parameter value(s) being monitored satisfy their respective criteria, then the same total acoustic power and HIFU exposure time used in the adjacent treatment site are used for the current treatment site, as represented by block 534. Treatment at the current treatment site is then commenced, as represented by block 536. If one or more of the tissue change parameter value(s) being monitored do not satisfy their respective criteria, then adjustments are made to the treatment variables for the current treatment site, as represented by block 538. In one embodiment, these adjustments are made by a manual adjustment of the operator of HIFU System 100. In one embodiment, these adjustments are made by HIFU System 100.

In one embodiment, a current treatment site may be skipped for direct HIFU Therapy due to the fact that it has already been treated indirectly by the HIFU Therapy applied to other (adjacent) treatment sites. A tissue change may have occurred at the current treatment site due to the treatment of proximate treatment sites. In general, HIFU induced tissue change areas grow toward the surface of the transducer if the total acoustic power (TAP) is high and HIFU on time is long enough. For example, when a HIFU Treatment is running with a 40 millimeter focal length transducer, the tissue changes will start to occur at a depth of about 40 millimeters. As the HIFU on time continues, the tissue change area grows toward to the surface of the transducer and may enter the pre-focal zone.

TCM readings will be positive when the tissue within the pre-focal region is heated and tissue change has occurred. Skipping the direct treatment of such regions will reduce overall treatment time.

Figure 13:
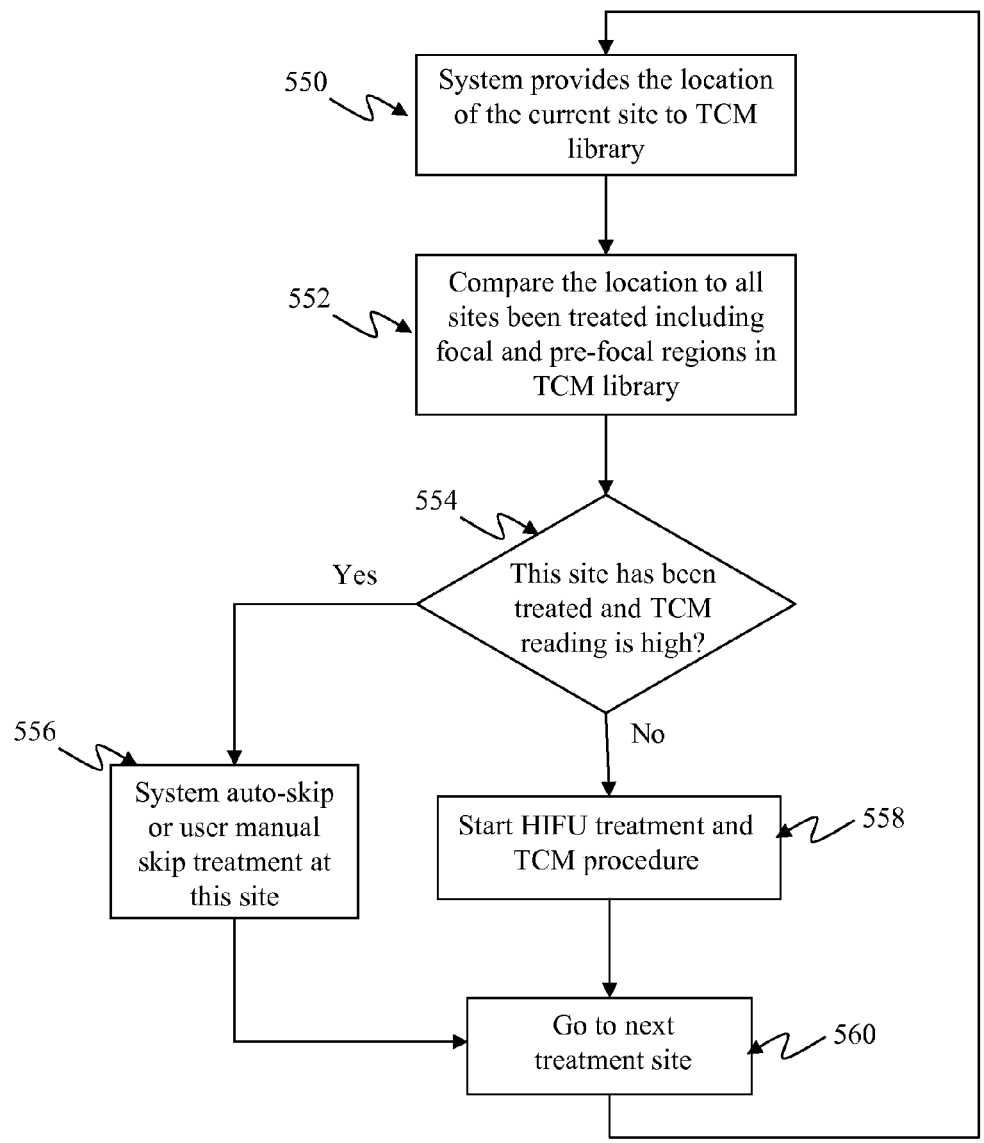
FIG. 13 is an exemplary method to determine whether a given treatment site has been sufficiently treated by indirect treatment

Referring to FIG. 13, a location of the current treatment site is determined, as represented by block 550. The BEFORE and AFTER images for the adjacent treatment sites are reviewed to determine the tissue change parameter value for the current treatment site, as represented by block 552. The tissue change parameter value for the current treatment site is then compared to a threshold value to determine if a sufficient tissue change has occurred due to the indirect treatment of the current treatment site, as represented by block 554. If a sufficient tissue change has occurred then the current treatment site may be skipped, as represented by block 556. If a sufficient tissue change has not occurred due to the indirect treatment of the current treatment site, the current treatment site is treated with HIFU Therapy, as represented by block 558. In one embodiment, the BEFORE image for this site is taken directly before treatment. In one embodiment, the BEFORE image for this site is the BEFORE image used for an adjacent treatment site. Once treatment at the current site has been completed, HIFU System 100 moves on to the next treatment site, as represented by block 560.

Figure 16:
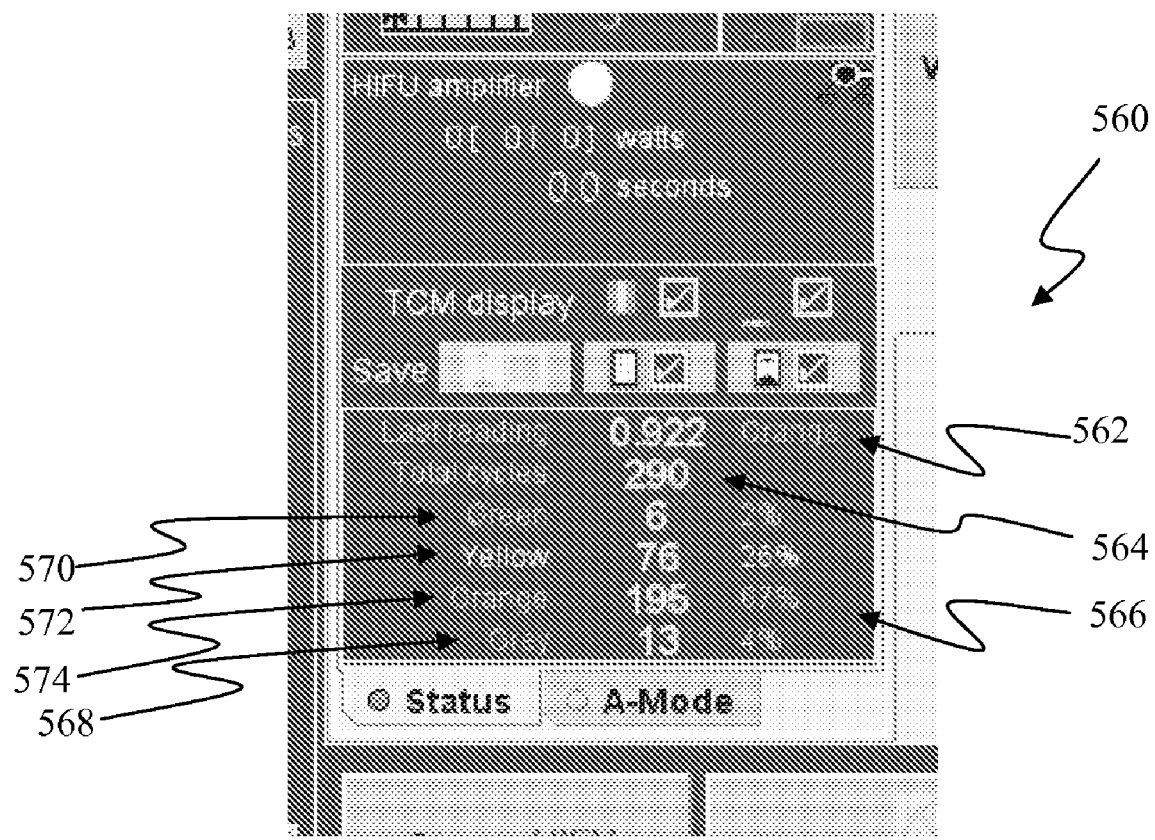
FIG. 16 is a detail view of the summary of FIG. 15.

In one embodiment, a statistical report of the tissue change parameter values for all treatment sites treated is provided on the display of HIFU System 100. Referring to FIG. 15, a statistical report 560 is shown and is shown in more detail in FIG. 16. Report 560 indicates the tissue change parameter value for the last treatment site 562, and the number of sites treated 564. In addition, a summary 566 of the classification of the tissue change parameter values for each treatment site is also provided. Summary 566 includes the number of sites for which the signal to noise ratio was not sufficient for tissue change monitoring (gray 568), the number of sites for which tissue change was not detected (green 570), the number of sites for which tissue change was detected (yellow 572), and the number of sites for which a large tissue change was detected (orange 574). An operator of HIFU System 100 may determine the success of the HIFU Treatment based on the percentages of sites in the yellow and orange categories. In one embodiment, the HIFU Treatment is likely successful if at least about 90 percent of the sites are in the yellow and orange categories.

The monitoring of a tissue change parameter for each treatment site provides feedback to an operator of changes to the tissue which might not be visible as echogenic changes via conventional ultrasound B-mode (2D brightness/echo) images. This permits the operator to have a better understanding of the current state of tissue 10 in the treatment region 12 and to modify one or more HIFU parameters (such as HIFU on time, HIFU off time, and total acoustic power) based on this understanding. As such, an operator may modify the treatment of upcoming treatment sites. In one embodiment, this modification may be made automatically by the software of HIFU System 100. The tissue change monitoring also provides an operator with a snapshot of sites that did not exhibit a sufficient amount of tissue change and, providing the possibility for the operator to revisit those sites to provide further HIFU exposure.

Tissue change monitoring also provides feedback of the success of the HIFU Treatment during treatment as opposed to traditional method of determining success, such as PSA nadir which make take weeks or months to know if the treatment was successful.

The tissue change monitoring examines a two dimensional region of interest to determine the degree of tissue change. Because tissue has non-uniform acoustic properties throughout the treatment region the tissue changes induced by HIFU may also have non-uniform formation. The two dimensional region of interest may capture much more information about the tissue change in the spatial domain than a single one-dimensional RF A-line. This will then provide a more accurate representation of the level of tissue change.

Although the invention has been described in detail with reference to certain illustrated embodiments, variations and modifications exist within the spirit and scope of the invention as described and defined in the following claims.

The invention claimed is:

1. An apparatus for treating tissue in a treatment region, the apparatus comprising:
   a transducer which is positionable relative to a tissue treatment area of a tissue, the transducer being configured to emit ultrasound energy and to sense ultrasound energy;
   a controller operably coupled to the transducer, the controller being configured to estimate changes in reflected backscattered energy in real-time for a plurality of regions of interest, wherein the estimated change in reflected backscattered energy corresponds to a tissue change value;
   the controller being further configured to operate the transducer in a pulse-echo mode prior to providing HIFU therapy to a first tissue treatment area, wherein imaging data is generated from the 2-D RF signals received from a first region of interest by the transducer;
   the controller being further configured to operate the transducer in a therapy mode wherein HIFU therapy is provided to the first tissue treatment area;
   the controller being further configured to operate the transducer in a pulse-echo mode after providing HIFU therapy to the first tissue treatment area, wherein imaging data is generated from the 2-D RF signals received from the first region of interest by the transducer; and
   the controller being further configured to analyze at least two 2-D RF signal data sets in the frequency domain, wherein the at least two 2-D RF signal data sets correspond to 2-D RF signals received from the first region of interest prior to and after the application of HIFU therapy, wherein the analysis of the at least two RF signal data sets includes determining the average power spectrum for each frequency band of the 2-D RF signals, wherein the plurality of frequency bands include a fundamental frequency band, a sub-harmonic frequency band, and a harmonic frequency band, wherein the maximum difference between the plurality of frequency bands of the at least two 2-D RF signals correspond to the estimated value of change in reflected backscattered energy for the region of interest.

2. The apparatus of claim 1, wherein the plurality of regions of interest include the tissue in the region between the transducer and the focal zone of the transducer, the tissue located in the region beyond the focal zone of the transducer, and the tissue located in the focal zone of the transducer.

3. The apparatus of claim 1, the controller being further configured to determine if a sufficient tissue change has occurred in the current tissue treatment area due to indirect HIFU treatment of the current tissue treatment area, wherein if a sufficient tissue change has occurred, the tissue treatment area is skipped.

4. The apparatus of claim 3, the controller being further configured to operate the transducer in a therapy mode wherein HIFU therapy is provided to the current tissue treatment area if sufficient tissue change has not occurred due to indirect HIFU treatment of the current tissue treatment area.

5. The apparatus of claim 1, the controller being further configured to provide additional HIFU therapy to a tissue treatment area where the tissue change value is low, wherein the treatment variables of the therapy mode may be modified for further treatment.

6. The apparatus of claim 1, the controller being further configured to determine if the signal to noise level of the received 2-D RF signal is sufficient to estimate changes in reflected backscattered energy, wherein if the mean of the absolute values of the 2-D RF signal is below a threshold, then the gain parameter is increased and the transducer is again operated in the pulse-echo mode and imaging data is generated.

7. The apparatus of claim 1, the controller being further configured to determine if the signal to noise level of the received 2-D RF signal is sufficient to estimate changes in reflected backscattered energy, wherein if the percentage of data points of the 2-D RF signal which are saturated is above a threshold, then the gain parameter is decreased and the transducer is again operated in the pulse-echo mode and imaging data is generated.

8. The apparatus of claim 1, wherein fine adjustments for independent gain control are provided for the transducer operating in the pulse-echo mode.

9. The apparatus of claim 1, further comprising a display for displaying the image generated after providing HIFU therapy to the first tissue treatment area, wherein the display includes a visual indicator of the tissue change value corresponding to the region of interest and the visual indicator is superimposed upon a location corresponding to the first tissue treatment area and preferably includes a color-coded visual indicator associated with the level of tissue change for the first tissue treatment area.

10. A method of treating tissue in a treatment region, the method comprising the steps of:
   estimating changes in reflected backscattered energy in real-time for a plurality of regions of interest, wherein the estimated change in reflected backscattered energy corresponds to a tissue change value;
   operating a transducer in a pulse-echo mode prior to providing HIFU therapy to a first tissue treatment area, wherein imaging data is generated from the 2-D RF signals received from a first region of interest by the transducer;
   operating the transducer in a therapy mode, wherein HIFU therapy is provided to the first tissue treatment area;
   operating the transducer in a pulse-echo mode after providing HIFU therapy to the first tissue treatment area, wherein imaging data is generated from the 2-D RF signals received from the first region of interest by the transducer;
   analyzing the at least two 2-D RF signal data sets in the frequency domain, wherein the at least two 2-D RF signal data sets correspond to 2-D RF signals received from the first region of interest prior to and after the application of HIFU therapy, wherein the analysis of the at least two 2-D RF signal data sets includes determining the average power spectrum for each frequency band of the 2-D RF signals, wherein the plurality of frequency bands include a fundamental frequency band, a sub-harmonic frequency band, and a harmonic frequency band, wherein the maximum difference between the plurality of frequency bands of the at least two 2-D RF signals correspond to the estimated value of change in reflected backscattered energy for the region of interest.

11. The method of claim 10, wherein the plurality of regions of interest include the tissue in the region between the transducer and the focal zone of the transducer, the tissue located in the region beyond the focal zone of the transducer, and the tissue located in the focal zone of the transducer.

12. The method of claim 10, further comprising the steps of determining if a sufficient tissue change has occurred in the current tissue treatment area due to indirect HIFU treatment of the current tissue treatment area, wherein if a sufficient tissue change has occurred, the tissue treatment area is skipped.

13. The method of claim 12, further comprising the steps of operating the transducer in a therapy mode wherein HIFU therapy is provided to the current tissue treatment area if sufficient tissue change has not occurred due to indirect HIFU treatment of the current tissue treatment area.

14. The method of claim 10, further comprising the steps of providing additional HIFU therapy to a tissue treatment area where the tissue change value is low, wherein the treatment variables of the therapy mode may be modified for further treatment.

15. The method of claim 10, further comprising the steps of determining if the signal to noise level of the received 2-D RF signal is sufficient to estimate changes in reflected backscattered energy, wherein if the mean of the absolute values of the 2-D RF signal is below a threshold, then the gain parameter is increased and the transducer is again operated in the puke-echo mode and imaging data is generated.

16. The method of claim 10, further comprising the steps of determining if the signal to noise level of the received 2-D RF signal is sufficient to estimate changes in reflected backscattered energy, wherein if the percentage of data points of the 2-D RF signal which are saturated is above a threshold, then the gain parameter is decreased and the transducer is again operated in the pulse-echo mode and imaging data is generated.

17. The method of claim 10, further comprising the steps of providing fine adjustments for independent gain control for operating the transducer in the pulse-echo mode.

18. The method of claim 10, further comprising the steps of displaying the image generated after providing HIFU therapy to the first tissue treatment area, wherein the image includes a visual indicator of the tissue change value corresponding to the region of interest and the visual indicator is superimposed upon a location corresponding to the first tissue treatment area and preferably includes a color-coded visual indicator associated with the level of tissue change for the first tissue treatment area.

* * * * *